(12) United States Patent
Aldrich et al.

(10) Patent No.: US 6,359,173 B1
(45) Date of Patent: *Mar. 19, 2002

(54) METHODS AND DEVICES FOR OXIDIZING A HYDROCARBON TO FORM AN ACID

(75) Inventors: Sharon M. Aldrich, Poulsbo; David C. DeCoster, Buckley, both of WA (US); Eustathios Vassiliou, Newark, DE (US); Mark W. Dassel, Indianola; Ader M. Rostami, Bainbridge Island, both of WA (US)

(73) Assignee: RPC Inc., Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/989,910

(22) Filed: Dec. 12, 1997

Related U.S. Application Data

(63) Continuation-in-part of application No. PCT/US97/10830, filed on Jun. 23, 1997, which is a continuation-in-part of application No. 08/876,692, filed on Jun. 16, 1997, which is a continuation-in-part of application No. 08/824,992, filed on Mar. 27, 1997, now Pat. No. 5,922,908, which is a continuation-in-part of application No. 08/812,847, filed on Mar. 6, 1997, now Pat. No. 6,288,270.

(60) Provisional application No. 60/020,798, filed on Jun. 24, 1996.

(51) Int. Cl.$^7$ .......................... C07C 51/31; B01J 10/00; C08G 63/02
(52) U.S. Cl. ...................... 562/543; 562/542; 422/129; 528/272
(58) Field of Search ............................... 562/542, 543; 422/129; 528/272

(56) References Cited

U.S. PATENT DOCUMENTS

| | | |
|---|---|---|
| 1,121,532 A | 12/1914 | Newberry |
| 2,014,044 A | 9/1935 | Haswell .......................... 75/17 |
| 2,223,493 A * | 12/1940 | Loder .......................... 260/537 |

(List continued on next page.)

FOREIGN PATENT DOCUMENTS

| | | | |
|---|---|---|---|
| DE | 4426132 A1 | 1/1996 | |
| DE | 4427474 A1 | 2/1996 | |
| EP | 439 007 A2 | 7/1991 | |
| EP | 729 084 A1 | 8/1996 | |
| EP | 729 085 A1 | 8/1996 | |
| EP | 751 105 A2 | 1/1997 | |
| FR | 2 722 783 A1 | 1/1996 | |
| GB | 415172 | 8/1934 | |
| GB | 738808 | 10/1955 | .......................... 2/3 |
| GB | 864106 | 3/1961 | |
| GB | 1143213 | 2/1969 | .................... 51/16 |
| GB | 2 014 473 A | 8/1979 | |
| JP | 48-003815 | 2/1973 | |
| WO | WO96/03365 | 2/1996 | |
| WO | WO 96/40610 | 12/1996 | |

OTHER PUBLICATIONS

Lewis, *Hawley's Condensed Chemical Dictionary*, 12$^{th}$ ed., *1993, pp. 7, 336, and 1076.
E. Sorribes et al., "Formación de neuvas fases en el proceso de obtención de ácido adípico: causas y efectos que provocan," Rev. R. Acad. Cienc. Exactas, Fis. Nat. Madrid *(1987), 81 (1), 233–5 (+ English language translation).
U.S. application No. 08/587,967, Dassel et al., filed Jan. 17, 1996.
U.S. application No. 08/812,847, Dassel et al., filed Mar. 6, 1997.
U.S. application No. 08/859,985, Vassiliou et al., filed May 21, 1997.
U.S. application No. 08/861,281, Dassel et al., filed May 21, 1997.
U.S. application No. 08/861,180, DeCoster et al., filed May 21, 1997.
U.S. application No. 08/861,176, Dassel et al., filed May 21, 1997.
U.S. application No. 08/859,890, Rostami et al., filed May 21, 1997.
U.S. application No. 08/861,210, Vassiliou et al., filed May 21, 1997.
U.S. application No. 08/824,992, Dassel et al., filed Mar. 27, 1997.
U.S. application No. 08/477,195 Dassel et al., filed Jun. 7, 1995.
U.S. application No. 08/876,692, Rostami et al., filed Jun. 16, 1997.
U.S. application No. 08/931,035, Dassel et al., filed Sep. 16, 1997.
U.S. application No. 08/934,253, DeCoster et al., filed Sep. 19, 1997.

*Primary Examiner*—Rosalynd Keys
(74) *Attorney, Agent, or Firm*—Seed Intellectual Property Law Group PLLC

(57) ABSTRACT

Methods and devices for controlling the reaction of a hydrocarbon to an acid by making phase-related adjustments are disclosed. In order to improve reaction rate and reactivity of the oxidation, a single phase at the operating temperature is attained and maintained by adjusting one or more of gaseous oxidant flow rate, pressure in the reaction zone, temperature in the reaction zone, feed rate of hydrocarbon, feed rate of solvent, feed rate of water if water is being fed, feed rate of the catalyst and other parameters. Methods and devices are also disclosed, wherein a hydrocarbon is reacted at a steady state with a gaseous oxidant to form an acid in a liquid mixture. The amount of water is maintained between a maximum level of water, over which maximum level the substantially single liquid phase is transformed to two liquid phases, and a minimum level under which catalyst precipitates. Further, methods are disclosed, wherein the temperature of the mixture is lowered to a point at which solid dibasic acid is precipitated, while maintaining a single liquid phase, and optionally all the catalyst in solution. At least part of the formed acid is then removed. The preferred hydrocarbon is cyclohexane, the preferred acid is adipic acid, the preferred solvent is acetic acid, and the preferred catalyst is cobalt(II) acetate tetrahydrate.

58 Claims, 9 Drawing Sheets

U.S. PATENT DOCUMENTS

| | | | |
|---|---|---|---|
| 2,223,494 A | 12/1940 | Loder | 260/586 |
| 2,301,240 A | 11/1942 | Baumann et al. | 183/115 |
| 2,439,513 A | 4/1948 | Hamblet et al. | 260/533 |
| 2,557,282 A | 6/1951 | Hamblet et al. | 260/533 |
| 2,565,087 A | 8/1951 | Porter et al. | 260/631 |
| 2,980,523 A | 4/1961 | Dille et al. | 48/215 |
| 3,161,603 A | 12/1964 | Leyshon et al. | 252/413 |
| 3,231,608 A | 1/1966 | Kollar | 260/533 |
| 3,234,271 A | 2/1966 | Barker et al. | 260/531 |
| 3,290,369 A | 12/1966 | Bonfield et al. | 260/537 |
| 3,361,806 A | 1/1968 | Lidov | 260/531 |
| 3,515,751 A | 6/1970 | Oberster et al. | 260/533 |
| 3,530,185 A | 9/1970 | Pugi | 260/586 |
| 3,613,333 A | 10/1971 | Gardenier | 55/89 |
| 3,677,696 A | 7/1972 | Bryk et al. | 23/2 |
| 3,839,435 A | 10/1974 | Shigeyasu et al. | 260/524 R |
| 3,928,005 A | 12/1975 | Laslo | 55/73 |
| 3,932,513 A | 1/1976 | Russell | 260/586 AB |
| 3,946,076 A | 3/1976 | Paasen et al. | 260/586 P |
| 3,957,876 A | 5/1976 | Rapoport et al. | 260/586 P |
| 3,987,100 A | 10/1976 | Barnette et al. | 260/586 P |
| 3,987,808 A | 10/1976 | Carbonell et al. | 137/3 |
| 4,025,498 A | 5/1977 | Buss et al. | 260/95 A |
| 4,032,569 A | 6/1977 | Onopchenko et al. | 260/533 C |
| 4,039,304 A | 8/1977 | Bechthold et al. | 55/10 |
| 4,055,600 A | 10/1977 | Langley et al. | 260/586 |
| 4,065,527 A | 12/1977 | Graber | 261/79 A |
| 4,158,739 A | 6/1979 | Schulz et al. | 562/543 |
| 4,263,453 A | 4/1981 | Schulz et al. | 562/543 |
| 4,308,037 A | 12/1981 | Meissner et al. | 55/10 |
| 4,332,590 A | 6/1982 | Smith | 23/230 A |
| 4,361,965 A | 12/1982 | Goumondy et al. | 34/57 R |
| 4,370,304 A | 1/1983 | Hendriks et al. | 422/224 |
| 4,394,139 A | 7/1983 | Board | 55/20 |
| 4,419,184 A | 12/1983 | Backlund | 162/49 |
| 4,423,018 A | 12/1983 | Lester, Jr. et al. | 423/243 |
| 5,061,453 A | 10/1991 | Krippl et al. | 422/106 |
| 5,104,492 A | 4/1992 | King et al. | 203/15 |
| 5,123,936 A | 6/1992 | Stone et al. | 55/8 |
| 5,170,727 A | 12/1992 | Nielsen | 110/346 |
| 5,221,800 A | 6/1993 | Park et al. | 562/543 |
| 5,244,603 A | 9/1993 | Davis | 261/87 |
| 5,270,019 A | 12/1993 | Melton et al. | 422/234 |
| 5,271,904 A | 12/1993 | Esposito et al. | 422/105 |
| 5,286,458 A | 2/1994 | Yang et al. | 422/168 |
| 5,294,378 A | 3/1994 | Succi et al. | 261/130 |
| 5,312,567 A | 5/1994 | Kozma et al. | 261/87 |
| 5,321,157 A | 6/1994 | Kollar | 562/543 |
| 5,374,767 A | 12/1994 | Drinkard et al. | 560/193 |
| 5,396,850 A | 3/1995 | Conochie et al. | 110/346 |
| 5,399,750 A | 3/1995 | Brun et al. | 562/553 |
| 5,463,119 A | 10/1995 | Kollar | 562/543 |
| 5,502,245 A | 3/1996 | Dassel et al. | 562/413 |
| 5,505,920 A | 4/1996 | Kollar et al. | 423/246 |
| 5,516,423 A | 5/1996 | Conoby et al. | 210/85 |
| 5,558,842 A | 9/1996 | Vassiliou et al. | 422/108 |
| 5,580,531 A | 12/1996 | Vassiliou et al. | 422/108 |
| 5,654,475 A | 8/1997 | Vassiliou et al. | 562/413 |
| 5,756,837 A | 5/1998 | Costantini et al. | 562/543 |

* cited by examiner

METHODS AND DEVICES FOR OXIDIZING A HYDROCARBON TO FORM AN ACID

CROSS-REFERENCE TO RELATED APPLICATIONS

This application is a continuation-in-part of PCT/US97/10830, filed Jun. 23, 1997, now pending; where this application and PCT/US97/10830 both claim priority to, and are both continuation-in-parts of U.S. application Ser. No. 08/876,692, filed Jun. 16, 1997, now pending; which claims priority to and is a continuation-in-part of U.S. application Ser. No. 08/824,992, filed Mar. 27, 1997, now U.S. Pat. No. 5,922,908 which claims priority to and is a continuation-in-part of U.S. application Ser. No. 08/812,847, filed Mar. 6, 1997, now U.S. Pat. No. 6,288,270 which claims the benefit of U.S. Provisional Application Ser. No. 60/020,798, filed Jun. 24, 1996.

TECHNICAL FIELD

This invention relates to methods and devices for making reaction products, and especially dibasic acids, by oxidizing a hydrocarbon under controlled conditions.

BACKGROUND ART

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process", the "Boric Acid Process", and the "Direct Synthesis Process", which involves direct oxidation of cyclohexane to adipic acid with oxygen in the presence of solvents, catalysts, and initiators or promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase". However, no attention has been paid so far to the importance of the two phases, except for separating the adipic acid from the "Polar Phase" and recycling these phases to the reactor partially or totally with or without further treatment.

It is also important to note that most studies on the Direct Oxidation have been conducted in a batch mode, literally or for all practical purposes.

There is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among the plethora of others, may be considered as representative of oxidation processes relative to the preparation of diacids and intermediate products.

U.S. Pat. No. 5,463,119 (Kollar), U.S. Pat. No. 5,374,767 (Drinkard et al.), U.S. Pat. No. 5,321,157 (Kollar), U.S. Pat. No. 3,987,100 (Barnette et al.), U.S. Pat. No. 3,957,876 (Rapoport et al.), U.S. Pat. No. 3,932,513 (Russell), U.S. Pat. No. 3,530,185 (Pugi), U.S. Pat. No. 3,515,751 (Oberster et al.), U.S. Pat. No. 3,361,806 (Lidov et al.), U.S. Pat. No. 3,234,271 (Barker et al.), U.S. Pat. No. 3,231,608 (Kollar), U.S. Pat. No. 3,161,603 (Leyshon et al.), U.S. Pat. No. 2,565,087 (Porter et al.), U.S. Pat. No. 2,557,282 (Hamblet et al.), U.S. Pat. No. 2,439,513 (Hamblet et al.), U.S. Pat. No. 2,223,494 (Loder et al.), U.S. Pat. No. 2,223,493 (Loder et al.), German Patent DE 44 26 132 A1 (Kysela et al.), and PCT International Publication WO 96/03365 (Constantini et al.).

None of the above references, or any other references known to the inventors disclose, suggest or imply, singly or in combination, oxidation reactions to intermediate oxidation products under conditions subject to the intricate and critical controls and requirements of the instant invention as described and claimed.

Our U.S. Pat. Nos. 5,580,531, 5,558,842, 5,502,245, as well as our PCT International Publication WO 96/40610 describe methods and apparatuses relative to controlling reactions in atomized liquids.

SUMMARY OF THE INVENTION

As aforementioned, the present invention relates to methods and devices of oxidizing a hydrocarbon, such as cyclohexane for example, to an acid, such as adipic acid for example. More particularly this invention pertains to a method of controlling in a first reaction zone the oxidation of a hydrocarbon to form an acid in the presence of a catalyst, a solvent, an optional initiator, water, and oxidation products; the hydrocarbon, the catalyst, the solvent, and at least part of the oxidation products forming at least partially a liquid mixture, the method characterized by the steps of:

(a) contacting the liquid mixture with a gaseous oxidant in the first reaction zone at a first temperature, the first temperature being adequately high for the oxidation to proceed;

(b) driving the oxidation to a steady state at a first hydrocarbon level, a first solvent level, a first catalyst level, and a first water level;

(c) controlling at least one of the first hydrocarbon level, the first solvent level, the first catalyst level, and the first water level, in a manner to cause formation of and/or maintain a single liquid phase in the first reaction zone, regardless of the presence or absence of a solid phase, and if necessary; and (d) making phase-related adjustments to the liquid mixture, the phase-related adjustments being at least partially based on phase formation relationships, when said liquid mixture is at a second temperature, and wherein the phase related adjustments are directed toward formation and/or maintenance of a single liquid phase.

The second temperature is preferably substantially the same as the first temperature. However, it may be different than the first temperature.

The phase related adjustments to the liquid mixture in the first reaction zone may be conducted by variable selected from a group consisting of temperature in the first reaction zone, pressure in the first reaction zone, gaseous oxidant flow rate into the first reaction zone, water flow rate into the first reaction zone, water removal rate from the first reaction zone, catalyst flow rate into the first reaction zone, hydrocarbon flow rate into the first reaction zone, hydrocarbon removal rate from the first reaction zone, solvent flow rate into the first reaction zone, solvent removal rate from the first reaction zone, recycled off-gas flow rate into the first reaction zone, and a combination thereof.

It is preferable that the method comprises a step of determining, one or more of:

a maximum hydrocarbon level, a maximum water level, and a maximum catalyst level, at or over which, the single liquid phase is transformed to two liquid phases; and a minimum solvent level, at or under which, the single liquid phase is transformed to two liquid phases;

under a set of conditions, wherein levels not being determined remain constant.

The step of determining one or more of the levels, at or over which, the single liquid phase is transformed to two liquid phases, may further comprise steps of:

obtaining a sample of a liquid mixture from the first reaction zone; and adding to the sample, hydrocarbon, or water, or catalyst, or a combination thereof, until a second liquid is formed.

The first hydrocarbon level, the first water level, and the first catalyst level are preferably controlled to be under the maximum hydrocarbon level, the maximum water level, and the maximum catalyst level, respectively, and the first solvent level is controlled to be maintained over the minimum solvent level.

The sample may be analyzed to obtain compositional data of the sample, and therefore of the contents of the reaction zone.

The compositional data of the sample may be compared with one or more of phase diagrams, thermodynamic data bases, flow sheets, computer flow sheet simulations, catalyst precipitation data, energy balances, and experimental data, and a step of making phase related adjustments and/or catalyst precipitation adjustments may be made in order to avoid formation of a second liquid phase, and/or catalyst precipitation, respectively, in the first reaction zone, if the comparison indicates that formation of a second liquid phase and/or catalyst precipitation are being approached.

The compositional data of the sample may also be compared with one or more of the maximum hydrocarbon level, the maximum water level, the maximum catalyst level, and the minimum solvent level, and then phase related adjustments may be made in the first reaction zone, if one or more of the maximum hydrocarbon level, the maximum water level, the maximum catalyst level, and the minimum solvent level, respectively, is being approached. If the additional hydrocarbon, or water, or catalyst necessary for formation of a second liquid phase is less than 10% by weight of the total hydrocarbon, or water, or catalyst contained in reaction zone or a sample from the reaction zone, then the maximum level of hydrocarbon or water or catalyst is being approached, and corrective measures have to be taken. Examples of such corrective measures are to reduce the first hydrocarbon level or the first water level or the first catalyst level, or increase the first solvent level, or a combination thereof. It is preferable that the additional hydrocarbon, or water, or catalyst necessary for formation of a second liquid phase should be controlled to be more than 10% (and in some cases—more than 20%) by weight of the total hydrocarbon or water or catalyst, respectively, contained in the reaction zone or a sample taken therefrom.

One or more of the first hydrocarbon level, the first catalyst level, and the first water level may be controlled to be maintained within a majority range, or a minority range. The majority range is defined as a range between a predetermined high majority level and a predetermined low majority level, the high majority level being lower than a maximum level at or over which maximum level a second phase is formed, the low majority level being between the high majority level and an average of the maximum level and a minimum level, at and under which minimum level catalyst recipitates. It is also preferable that the high majority level is close to the level at which a second phase formation is being approached.

In other occasions, it may be preferable that the first water and/or the first solvent level is controlled to be maintained within a minority range, the minority range being a range between a predetermined low minority level, and a predetermined high minority level, the low minority level being higher than a minimum level at or under which catalyst precipitates, and the high minority level being between the low minority level and an average of the minimum level and a maximum level, at and over which maximum level a second phase is formed.

The high importance of controlling the miscellaneous levels within the majority and/or minority ranges, is that within these ranges unintentional and/or accidental formation of a second liquid phase or catalyst precipitation is minimized, if not eliminated. Depending on each individual case, and the degree of achievable control, the majority and minority high and low levels may be predetermined.

The first temperature may be controlled by evaporating condensible volatile matter from the reaction zone, and recirculating at least part of the condensible volatile matter to the reaction zone as condensate.

The methods and devices of the present invention are particularly suitable in the case that the acid comprises adipic acid, the hydrocarbon comprises cyclohexane, the solvent comprises acetic acid, the catalyst comprises a cobalt salt, and the optional initiator comprises a compound selected from a group comprising acetaldehyde, cyclohexanone, and a combination thereof.

The methods of this invention may also comprise a step of controlling at least one level of the first water level, and the first solvent level in a manner to be higher than a respective level, at or under which, catalyst precipitates; and the first hydrocarbon level, and the first catalyst level to be lower than a respective level, at or over which, catalyst precipitates.

The above methods may further comprise steps of:

taking a sample from the first reaction zone;

lowering the temperature of the sample to a predetermined second temperature, and if a second liquid phase is formed at a critical temperature in the range between the first and second temperatures, either decrease in the first reaction zone the first level of one component selected from a group consisting of hydrocarbon, water, catalyst, and a mixture thereof to a degree that in a new sample a second liquid phase does not form in the range between the first and second temperatures, or increase in the first reaction zone the first solvent level to a degree that in a new sample a second liquid phase does not form in the range between the first and second temperatures, or increase in the first reaction zone the first temperature to a third temperature by at least the difference between the critical temperature and the second temperature, or a combination thereof.

It is preferable that controlling the first water level within the upper and lower limits (maximum water level over which a second liquid phase forms, and minimum water levels under which catalyst precipitates, respectively) is based on determining the composition of the single-phase liquid mixture of the first reaction zone, comparing said composition with one or more of phase diagrams, thermodynamic data bases, flow sheets, computer flow sheet simulations, catalyst precipitation data, energy balances, and experimental data, and adding water to the single-phase liquid mixture in the first reaction zone if the lower limit is being approached or removing water from the first reaction zone if the upper limit is being approached.

The methods of this invention may also comprise a combination of the following steps:

taking a sample from the first reaction zone;

confining the sample within a closed cell under adequate pressure to retain the sample in a substantially liquid form;

raising the cell temperature from the first temperature to a higher temperature; and if catalyst precipitates within a predetermined rise in temperature;

raising the level of water or the level of solvent in the first reaction zone, or lowering the level of hydrocarbon or the level of catalyst in the first reaction zone.

In a different version of the instant invention, the methods may comprise a combination of the following steps:

taking a sample from the first reaction zone;

confining the sample within a closed cell under adequate pressure to retain the sample in a substantially liquid form;

adding hydrocarbon to the sample to determine if catalyst precipitates before formation of a second phase; and controlling in the first reaction zone the first hydrocarbon level to be maintained at a level lower than the level required to cause catalyst precipitation at levels of solvent, catalyst, and water present in the cell.

The methods of this invention may also comprise steps of:

lowering the first temperature of the reaction mixture to a second temperature, while maintaining a single liquid phase at the second temperature; and removing at least part of the formed acid.

The above method may further include the step of recycling at least part of one or more of products, intermediates, by-products, reactants, solvents, off-gases, and other existing ingredients either directly to the first reaction zone or indirectly after post-treatment, or a combination thereof.

The lowering of the first temperature of the reaction mixture to the second temperature may be performed at least partially by an operation selected from a group consisting of: (a) evaporating of at least part of the hydrocarbon, (b) lowering the first pressure to a second pressure, (c) adding matter having a temperature lower than the first temperature, (d) adding volatile matter, such as cyclohexane for example, (e) removing heat by external means, (f) removing a first amount of heat by any suitable means, and adding a second amount of heat by external means, the first amount of heat being greater than the second amount of heat, and (g) a combination thereof.

Maintaining a single liquid phase at the second temperature may be controlled by adjusting the level of hydrocarbon, or water, or solvent, or a combination thereof, at the second temperature. The lowering of the first temperature to a second temperature may be preferably conducted in a second zone. The lowering of the first temperature to the second temperature may involve an intermediate step of lowering the first temperature to a first intermediate temperature by lowering the first pressure to an intermediate pressure to form a first intermediate liquid phase containing no substantial amount of solid phase.

The methods and devices of the present invention are particularly suitable in the case that the acid comprises adipic acid, the hydrocarbon comprises cyclohexane, the solvent comprises acetic acid, the catalyst comprises a cobalt salt, and the optional initiator comprises a compound selected from a group comprising acetaldehyde, cyclohexanone, and a combination thereof.

At least part of one or more of products, intermediates, by-products, reactants, solvents, off-gases, and other existing ingredients may be recycled either directly to the first reaction zone or indirectly after post-treatment, or in a combination thereof.

In any of the above-recited methods, there may be further included the step of comparing compositional data of the liquid mixture with one or more of phase diagrams, thermodynamic data bases, flow sheets, computer flow sheet simulations, catalyst precipitation data, energy balances, and experimental data, and a step of making phase related adjustments and/or catalyst precipitation adjustments in order to avoid formation of a second liquid phase, and/or catalyst precipitation, respectively, in the first reaction zone, if the comparison indicates that formation of a second liquid phase and/or catalyst precipitation are being approached.

In any of the above-recited methods, there may further include the step of reacting adipic acid with a reactant selected from a group consisting of a polyol, a polyamine, and a polyamide in a manner to form a polymer of a polyester, or a polyamide, or a (polyimide and/or poyamideimide), respectively. The invention may further include the step of spinning the polymer into fibers.

The instant invention also relates to a reactor device for oxidizing a hydrocarbon, the hydrocarbon being at least partially in a liquid state, with a gaseous oxidant to form an acid, the device comprising:

a first reaction chamber;

a temperature monitor connected to the reaction chamber for measuring temperature inside said reaction chamber;

phase detection means for detecting phase-related characteristics of ingredients within the first reaction chamber; and phase control means for making phase-related adjustments and controlling the phase characteristics of said ingredients within the first reaction chamber, if so desired.

The phase control means may further comprise temperature control means for controlling the first temperature. The phase control means may further comprise correlation means for correlating compositional data of the liquid mixture with one or more of phase diagrams, thermodynamic data bases, flow sheets, computer flow sheet simulations, catalyst precipitation data, energy balances, and experimental data, and making phase related adjustments and/or catalyst precipitation adjustments in order to avoid formation of a second liquid phase, and/or catalyst precipitation, respectively, in the first reaction zone, if the correlation indicates that formation of a second liquid phase and/or catalyst precipitation are being approached.

The phase detection means may provide information to the phase control means for adjusting feeding rates of ingredients fed to the reaction chamber toward formation or maintenance of a single liquid phase.

The reactor device of the present invention may also comprise variable control means for controlling in the reaction chamber a variable selected from a group consisting of temperature in the first reaction chamber, pressure in the first reaction chamber, gaseous oxidant flow rate into the first reaction chamber, water flow rate into the first reaction chamber, water removal rate from the first reaction chamber, catalyst flow rate into the first reaction chamber, hydrocarbon flow rate into the first reaction chamber, hydrocarbon removal rate from the first reaction chamber, solvent flow rate into the first reaction chamber, solvent removal rate from the first reaction chamber, recycled off-gas flow rate into the first reaction chamber, and a combination thereof.

The reactor device may also comprise:
liquid feeding means for feeding at least partially hydrocarbon, solvent, catalyst, optionally initiator, and optionally water into the first reaction chamber;
water removing means for removing water from the first reaction chamber;
gaseous feeding means for feeding oxidant into the first reaction chamber; and
water level control means for controlling the water level in the reaction chamber in a range between a maximum level of water, over which maximum level the substantially single liquid phase is transformed to two liquid phases, and a minimum level under which catalyst precipitates.

The water level control means may comprise water level detection means for detecting positioning of the water level with respect to the maximum level and the minimum level.

The reactor device may also comprise a controller connected to the water level detection means for receiving information regarding the positioning of the water level, and using said information for adjusting said water level in a manner to control said water level between the maximum level and the minimum level in the reaction zone.

The water level detection means may comprise a temperature operated detector, or a water-addition operated detector, or both for detecting the positioning of the water level with respect to the minimum level and the maximum level, respectively. Further, the water level control means may comprise an analytical water level detection means for detecting and/or determining the water level in the first reaction chamber, and wherein the reactor device further comprises a controller connected to the analytical water level detection means for receiving information regarding the water level in the reaction chamber, comparing said information with one or more of phase diagrams, thermodynamic data bases, flow sheets, computer flow sheet simulations, catalyst precipitation data, energy balances, and experimental data stored in the controller, and using said comparison for adjusting said water level in the first reaction chamber in a manner to control said water level between the maximum level and the minimum level.

The reactor device may further comprise a distillation column or a condenser, connected to an off-gas line exiting the first reaction chamber. A decanter or retaining chamber may be connected to the condenser.

The water level detection means may comprise a temperature operated detector for detecting the positioning of the water level with respect to the minimum level, and/or a water-addition operated detector for detecting the positioning of the water level with respect to the maximum level.

The reactor device may also comprise:
first temperature control means connected to the first reaction chamber for controlling temperature in said first reaction chamber;
first pressure control means connected to the first reaction chamber for controlling pressure in said first reaction chamber;
first hydrocarbon feeding means connected to the first reaction chamber for feeding hydrocarbon into said first reaction chamber;
first gaseous oxidant feeding means connected to the first reaction chamber for feeding gaseous oxidant into said first reaction chamber;
a second chamber connected to the first reaction chamber;
second temperature control means connected to the second chamber for controlling the temperature in said second chamber;
second pressure control means connected to the second chamber for controlling the pressure in said second chamber;
a controller for controlling miscellaneous parameters in the chambers in a manner that in the second chamber there is a single liquid phase.

A condenser(s) or distillation column(s) may be connected to the first reaction chamber and to the second chamber. A retaining chamber(s) or decanter(s) may be connected to the condenser(s).

The reactor device may further comprise a first intermediate chamber communicating with the first reaction chamber;
a first intermediate chamber communicating with the first reaction chamber;
first intermediate temperature control means connected to the first intermediate chamber for controlling the temperature in said first intermediate chamber;
first intermediate pressure control means connected to the intermediate chamber for controlling the pressure in said first intermediate chamber;
first intermediate external heating means for providing thermal energy to matter inside the first intermediate chamber;
a condenser connected to the first intermediate chamber;
separating means connected to or being part of the second chamber for separating at least partially the dibasic acid from the mixture.

It may further comprise:
a second intermediate chamber connected to the first intermediate chamber and the second chamber;
second intermediate external cooling means for removing thermal energy from matter inside the second intermediate chamber.

A second phase control means may be connected to the second chamber for ensuring the existence of one single liquid phase in the second chamber. Also, a catalyst precipitation control means may be connected to the second chamber for ensuring the absence of precipitated catalyst in the second chamber.

Under certain circumstances, at least two of the chambers may be one and the same unit.

One or more of the reaction chambers or other chambers, may be of the atomization or the stirred-reactor type.

In any of the above described chambers, means for adding heat by internal or external means, removing heat by internal or external means, adding volatile matter, removing volatile matter, controlling temperature, controlling pressure, etc., may be incorporated.

In the embodiments described herein, the amount of water present includes amounts of water introduced by other means, such as the crystalline water of cobalt(II) acetate tetrahydrate, for example, unless otherwise specified. In the case that the water, such as crystalline water for example, is not accounted for as being part of the water level, then it is accounted for as being part of the entity that it introduces it, such as catalyst for example. This invention encompasses both cases. Control may be achieved by either taking into account additional water, such as for example the crystalline water of the catalyst, or by not accounting for such additional water, depending on the particular situation.

By the term "steady state" it is meant that the reaction has reached an equilibrium, which equilibrium, however, may be adjusted periodically or continuously in order to achieve a desired result. If for example more water is needed in the reaction zone to avoid catalyst precipitation, the water feed rate to the reaction zone may be increased appropriately, and still the reaction may be considered to be at a "steady state". Similarly, if less water is needed to avoid formation of two phases, the water feed rate to the reaction zone may be decreased appropriately, and still the reaction may be considered to be at a "steady state".

The terms "substantially single-phase liquid", "substantially single liquid phase" "single liquid phase", and "single phase" are for all practical purposes synonymous for the purposes of this invention. They all intend to indicate that there is no second liquid phase present, while a solid phase may or may not be present. The terms "second phase formation" or "formation of a second phase" refer to a second liquid phase, and not to a solid phase, unless otherwise specified.

The term "level" of an ingredient (reactant, reaction product, inert matter, or any other type of matter present) includes both "relative level" and "percentage level". According to the instant invention, both methods and devices may perform by using either one or the other type of "levels". In some occasions it may be easier to use one type rather than the other. "Relative level" of an ingredient denotes the amount of the ingredient present in weight units or in volume units, in a reaction zone or in a cell for example, as compared to 100 units, in weight units or in volume units, respectively, of the rest of the ingredients present, or the rest of the ingredients under consideration. The rest of the ingredients present or the rest of the ingredients under consideration, in this case, have a constant ratio with respect to each other. On the other hand, "percentage level" is the level expressed as a percentage based on total amount of all or of a desired number of specific ingredients. The percentages may be expressed also either by weight or by volume.

A controller, preferably a computerized controller, may handle with ease and accuracy either type of "level". Programming a computerized controller to perform such functions is a routine process, well known to the art. According to this invention, a controller, based on information received, from a reaction zone for example, controls feed rates, temperatures, pressures, and other parameters in order to achieve the desirable results. Since the raw results regarding the point of a second liquid phase formation (which results are received from a cell, such as the cells shown in FIGS. 2, 2A, and 2B, which will be discussed in detail at a later section) are obtained in relative levels, maintenance or adjustments in the reaction zone are more accurate when "relative levels" are used. The controller may also be programmed, by well known to the art techniques, to include flow sheet simulation, which may account for vapor/liquid equilibrium and energy balance effects.

BRIEF DESCRIPTION OF THE DRAWINGS

The reader's understanding of this invention will be enhanced by reference to the following detailed description taken in combination with the drawing figures, wherein.

DETAILED DESCRIPTION OF THE INVENTION

Figure 1:
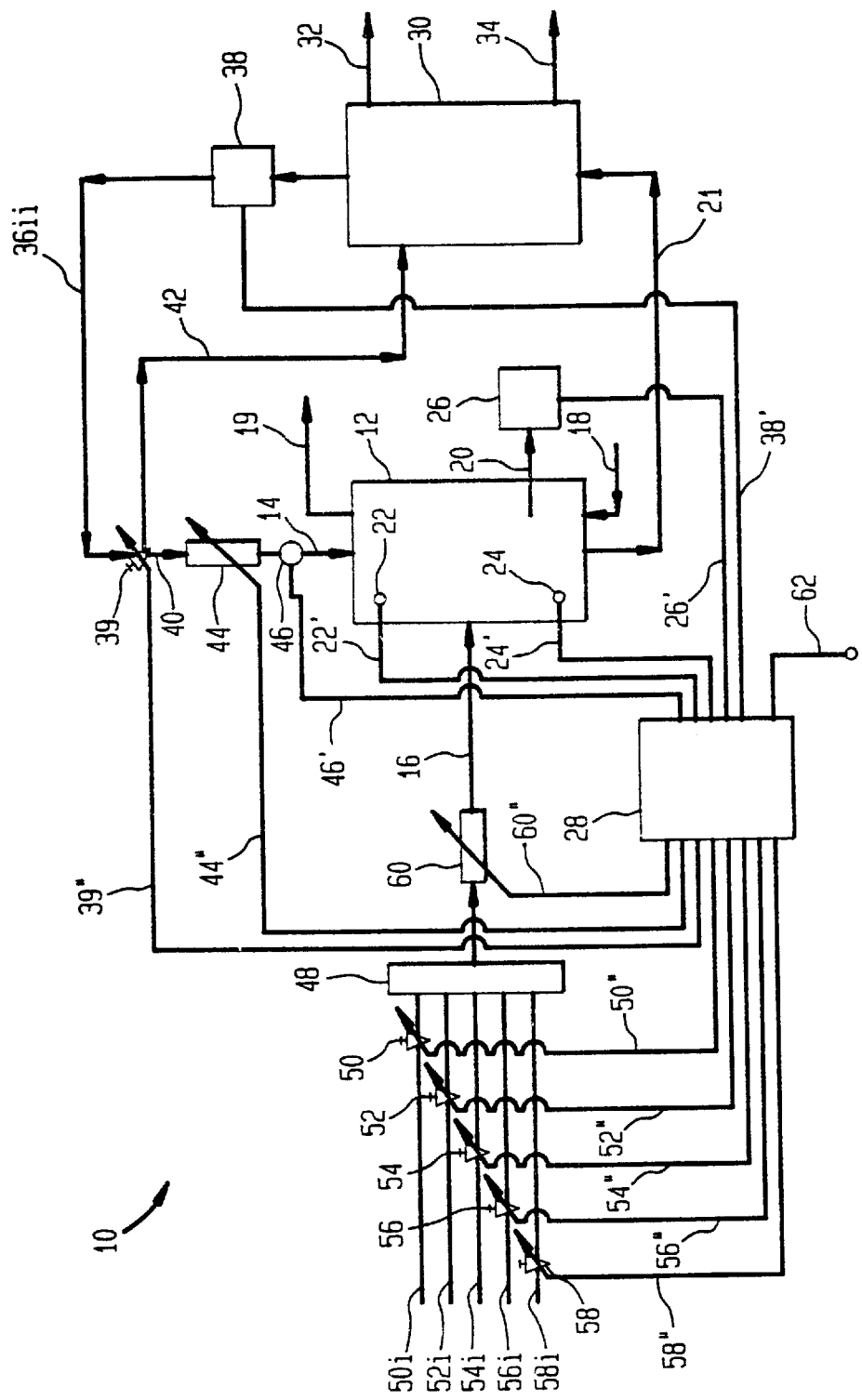
FIG. 1 illustrates schematically a preferred embodiment of the present invention.

As mentioned earlier, this invention relates to methods of making intermediate oxidation products, such as acids, for example, by oxidizing a hydrocarbon with a gas containing an oxidant, preferably oxygen.

A tubular rocking mini-reactor containing steel balls was used for a series of experiments. The steel balls were added to provide highly enhanced surface factor by means of distributing a thin film on the surface of the steel balls. Surface factor is defined in this case as the ratio of the surface of the liquid/gas interface per unit volume of the liquid. The mini-reactor comprised a tubular stainless steel body having an inside diameter of $^{23}/_{32}$", an outside diameter of 2¼", an outside length of about 11½", and an inside length of about 9½". The total capacity of the mini-reactor was 75 cc. Approximately 890 stainless steel balls having a diameter of ⅛" were used in the mini-reactor as agitation and mixing means, along with a rocking action of ±33 degrees from horizontal at a frequency of 10 cycles per minute, unless otherwise stated. The mini-reactor had a screw cap top, a number of thermocouples inside and outside for measuring and controlling the temperature. It was surrounded by heating tape, and insulated by glass fiber. It had ports for feeding gases and liquids. It was also provided with a pressure transducer. Both temperature and pressure were recorded and controlled through a computer using supervisory control software.

In operation of the mini-reactor, the following procedure was followed, unless otherwise stated. The system was initially purged with nitrogen, the feed was added, while purging with nitrogen, through the top of the mini-reactor which was in an uncapped position, the mini-reactor was capped and purged again with nitrogen to a pressure of about 50 psig, the temperature was raised to a desired degree (usually 100–105° C. ), the pressure was brought to about 100 psig with nitrogen, and the oxygen was introduced to a pressure of an additional 100 psig, thus bringing the total pressure to about 200 psig. The pressure (P) and the rate of pressure drop (dP/dt), among other variables were then recorded. Unless no substantial reaction takes place, the dP/dt goes from substantially zero rate to a maximum, and then it drops off again to substantially zero rate. In the different plots or Tables, when the terms "reaction rate" and "reactivity" are used, they correspond to the maximum dP/dt in each particular case, unless otherwise stated. An initial sharp peak preceding the maximum is disregarded, as it is believed to correspond to a fast oxidation of the initiator, such as acetaldehyde for example. In the case that cyclohexanone is used as initiator, such a preceding peak is not as sharp or pronounced. Although the terms "promoter" and "initiator" are many times used in the literature and in this work interchangeably to mean "initiator", the more strict meaning of the term "initiator" should be used for a substance which decreases the reaction initiation period, such as acetaldehyde or cyclohexanone, or methylethylketone, for example, and the term "promoter" should be used for a substance that promotes the reaction, such as bromide ions in the case of producing terephthalic acid from p-xylene, for example.

The inventors also used a high pressure, agitated, glass tube to determine phase relationships under conditions of actual reaction temperature, pressure, and composition.

Analysis of the products of reaction was conducted by HPLC and GC, both being well known to the art techniques.

After a reaction has taken place in the Direct Synthesis of cyclohexane to adipic acid, a mixture of two liquid phases is present at ambient temperature, along with a solid phase mainly consisting of adipic acid. The two liquid phases have been called the "Polar Phase" and the "Non-Polar" phase. However, no attention has been paid so far to the importance of the two phases, except for separating the adipic acid from the "Polar Phase" and recycling these phases to the reactor partially or totally with or without further treatment.

The inventors of the instant invention, using the above apparatus, unexpectedly discovered that both the composition and a number of relationships between the "Polar" and the "Non-Polar" phases are of utmost importance for the reactions taking place during the Direct Synthesis. They also found out that not only the relationship of the phases at reaction temperature are important, but also even data on the relationship of the phases at room temperature may be utilized to control the reaction at reaction temperatures, which is totally unexpected, since the phase relationship may change drastically with temperature.

According to the present invention, "Polar Phase" is a liquid phase which contains predominantly polar components, while "Non-Polar Phase" is a liquid phase which contains predominantly non-polar components. In addition, when two liquid phases are present, the one which is more polar than the other is the "Polar Phase" while the one which is less polar is the "Non-Polar Phase". Under certain controlled circumstances, as explained in more detail below, the two phases may merge into one phase, which is called "Single Phase", according to this invention. The "Single Phase" may be a "Single Polar Phase" if it contains predominantly polar components, or a "Single Non-Polar Phase" if it contains predominantly non-polar components. Further, as the temperature increases, one of the two phases may increase and the other decrease. If the "Polar Phase" decreases in a manner to finally be absorbed by the "Non-Polar Phase", then the "Single Phase" formed is a "Single Non-Polar Phase". Similarly, if the "Non-Polar Phase" decreases in a manner to finally be absorbed by the "Polar Phase", then the "Single Phase" formed is a "Single Polar Phase". Regardless of the type of the phase, "RT" phase is a phase as it exists at ambient or room temperature; "75° C." phase is a phase as it exists at 75° C. ; "100° C." phase is a phase as it exists at 100° C., and so on and so forth. Ambient or Room Temperature is about 20° C. When mentioning phases in this discussion, implied reference is made to liquid phases, unless solid phases are specifically cited and stated as such.

For purposes of clarity and brevity, the most preferred constituents may be used to exemplify the methods of the present invention, instead of more generic terms. For example "acetic acid" may be used instead of "solvent", but it should be understood that any other suitable solvent(s) may be used in said methods. Examples of less preferred solvents are butyric acid, propionic acid, etc. In a similar manner, "acetaldehyde" may be used instead of the more generic name "promoter", and "cobalt acetate tetrahydrate", or "cobalt acetate" (both meaning "cobaltous acetate tetrahydrate" unless otherwise specified) may often be used instead of the more generic term "catalyst".

In addition to the formation of adipic acid, the methods of the present invention may also be applied to other monobasic or dibasic acids from the corresponding cyclic aliphatic hydrocarbons or aromatic hydrocarbons. Examples are formation of glutaric acid from cyclopentane, formation of pimelic acid from cycloheptane, and the like. Further the teachings of this invention may be used for the formation of benzoic acid from toluene, formation of phthalic acid from o-xylene, formation of isophthalic acid from m-xylene, formation of terephthalic acid from p-xylene, and the like.

Since quantity-wise, the major polar component in the reaction mixture is acetic acid having a specific gravity slightly higher than 1 g/cc, and the major non-polar component is cyclohexane having a specific gravity slightly lower than 0.8 g/cc, the polar phase is heavier than the non-polar phase, and if both are present, the non-polar phase tends to move toward the top, while the polar phase tends to move toward the bottom. Thus, in a test tube if a sample has a polar phase and a non-polar phase, the polar phase will reside at the bottom of the tube, and the non-polar phase will reside at the top of the tube.

It was observed by the inventors that addition of very small amounts of water, as well as small changes in the amount of cobalt(II) acetate tetrahydrate, have a substantial effect on the relationship of the two phases. It is speculated that this occurs because water and cobalt(II) acetate tetrahydrate are very polar compounds.

For example, the composition of Table 1 was found to be in the form of two phases at room temperature. The bottom phase, which is the RT polar phase constituted only about 3% (by volume) of the total, while the RT non-polar phase constituted about 97% (by volume) of the total. At this point it is very important to note that substantially the total amount of the catalyst, as determined calorimetrically, resided in the bottom polar phase. For example, in this instance, the top phase was colorless and clear, while the bottom phase had a dense magenta coloration.

As shown in Tables 2 and 3, after adding about only 0.4% (by weight) water to the composition represented in Table 1, the volume of the RT polar phase grew to about 17% (by volume). As more and more water was added, the RT polar phase increased further, and at about 6% (by weight) water, the RT polar phase constituted about 30% (by volume) of the total. The initial addition of water had considerably higher effect in the increase of RT polar phase than the addition of further amounts of water. However, at low concentrations of cyclohexane and higher concentrations of acetic acid, the water has a considerably lower effect on the ratio of the two phases. During the reaction of cyclohexane with oxygen, a considerable amount of water is produced, and therefore, the presence of water is a fact, and not a matter of choice.

By adding a small amount (about 0.4 to about 1% by weight) of water an appreciable amount of RT polar phase was formed (about 20% by volume). Then, by separating the two phases, and re-mixing them in different proportions to form the totality of a reaction feed mixture, it was found unexpectedly that, in the case of the mini-reactor, the reactivity of the mixture was proportional to the amount of the RT polar phase present, to a certain point and then it dropped. This drop in the batch type mini-reactor may be due to cyclohexane starvation.

TABLE 1

COMPOSITION OF STOCK SOLUTION

| INGREDIENTS | GRAMS | WT % | MOLE % |
|---|---|---|---|
| Cobalt (II) Acetate Tetrahydrate | 0.34 | 0.71 | 0.21 |
| Acetic Acid | 14.68 | 30.58 | 38.09 |
| Acetaldehyde | 0.34 | 0.71 | 1.20 |
| Cyclohexane | 32.64 | 68.00 | 60.49 |
| Total | 47.00 | | |

TABLE 2

FEED SOLUTIONS CONTAINING DIFFERENT AMOUNTS OF WATER

| Graduated Cylinder # | | i | ii | iii | iv | v | vi |
|---|---|---|---|---|---|---|---|
| Wt of Empty Cylinder | gm | 52.34 | 34.59 | 34.26 | 35.60 | 39.03 | 34.94 |
| Wt of Cylinder + Stock Solution | gm | 57.39 | 39.74 | 39.44 | 40.97 | 44.49 | 40.13 |
| Wt of the feed solution | gm | 5.06 | 5.15 | 5.18 | 5.36 | 5.46 | 5.19 |
| Wt of Cylinder + Feed Soln. + Water | gm | 57.39 | 39.76 | 39.49 | 41.07 | 44.68 | 40.48 |
| Wt of Water added | gm | 0.00 | 0.02 | 0.05 | 0.11 | 0.19 | 0.35 |
| Wt % of Water added | | 0.00 | 0.41 | 0.94 | 1.92 | 3.36 | 6.33 |

TABLE 3

VOLUME OF RT POLAR (BOTTOM) PHASE AS COMPARED TO RT NON-POLAR (TOP) PHASE

| Graduated Cylinder # | | i | ii | iii | iv | v | vi |
|---|---|---|---|---|---|---|---|
| Volume (ml) before adding water | Top Phase | 6.3 | 6.2 | 6.2 | 6.4 | 6.3 | 6.4 |
| | Bottom Phase | 0.2 | 0.2 | 0.2 | 0.3 | 0.3 | 0.3 |
| Volume (ml) after adding water | Top Phase | 6.3 | 5.3 | 5.1 | 5.3 | 5.0 | 4.8 |
| | Bottom Phase | 0.2 | 1.1 | 1.3 | 1.4 | 1.8 | 2.0 |
| Volume % of the bottom Phase | Before Water addition | 3.1 | 3.1 | 3.1 | 4.5 | 4.6 | 4.5 |
| | After Water addition | 3.1 | 17.1 | 20.31 | 20.9 | 26.5 | 29.4 |

It was also observed that at a level of about 20% RT polar phase, specifically in case iii of Table 3, as the temperature increased, the polar phase progressively shrank to a very small volume, and finally it disappeared into the non-polar phase at a temperature of about 100° C. The consequence of this was that as the polar phase (which as mentioned before contains most if not substantially all the catalyst) shrank between 80° and 100° C., at some point it became over-saturated with catalyst, which resulted in catalyst precipitation. This is highly undesirable not only because of the highly decreased availability of catalyst, but also because precipitated matter in a reactor causes loss of reactor and plant utility, and high maintenance cost due to plugging of lines, etc. Upon further heating of the solution under vigorous agitation, at about 100° C., a single non-polar phase was formed, and most of the precipitated catalyst re-dissolved in the single non-polar phase, while some remained still in the precipitated form. Thus, in this particular case, although a reaction of cyclohexane with oxygen may proceed at temperatures lower than 100° C., the reaction rate and reactivity would be considerably reduced, since the dissolved catalyst level has been reduced, because the catalyst was either dissolved in a very small polar phase, or precipitated. Another consequence of this is that unless one uses a temperature of 100° C., or higher, in this particular case, it is very difficult to bring in contact the bulk of the material, which is the non-polar phase, containing substantially all the cyclohexane available, with the catalyst, all of which substantially resides in the very small amount of the polar phase, and with the gaseous phase of oxygen. Water concentration in the reactor, due to water formation, greater than the one represented by cases ii and iii in Table 3, will significantly worsen the aforementioned deleterious effects. Higher temperatures may not always be a practical remedy for these problems, because in order to improve chemical yield it may be advantageous to run the reaction at lower temperatures.

At different relatively low proportions of RT polar phase to RT non-polar phase (about less than 30% or 40% polar phase, in this particular case), there is a phase-critical or phase transition temperature, below which two liquid phases are formed, and the polar phase, containing most, if not substantially all the catalyst present, causing the reaction rate and reactivity to suffer considerably. It is therefore important to run the reaction at or above that temperature. It is more preferable to run the reaction at temperatures at least 5° C. above the phase-critical temperature or phase transition temperature. For different compositions, the phase-critical temperature will vary, but it is very easy to be determined by using a high-pressure, agitated, transparent glass vial, in which the sample is introduced, and the temperature is raised with simultaneous observation of the phase changes.

It should be stressed that as the amount of water present in the composition increases, the shrinkage upon heating of the polar phase decreases, and finally the two phases do not become a single phase, even at elevated temperatures, even at temperatures higher than the desirable reaction temperatures. Thus, in order to attain a single phase, it is preferable that water and/or hydrocarbon are controlled by removal (water and hydrocarbon increase the phase-critical temperature), or the amount of solvent increased (solvent decreases the phase-critical temperature). As the amount of acetic acid increases in a composition (including both polar and non-polar phases), the composition can withstand the presence of more water without formation of two liquid phases within the range of desirable reaction temperatures.

It was also observed that at about 65% RT polar phase, as the temperature increased, the non-polar phase shrank, and at a temperature of 97° C., it was completely absorbed by the polar phase to form a single polar phase, as defined earlier. Further, it was observed that at higher amounts of water present (about 7% by weight of the total composition), the presence of two liquid phases persisted even at 120° C. Thus, it is preferable that the reaction is run in a manner that the amount of water remains adequately low (or removed), so that the formation of two phases at the operating temperature is avoided.

As mentioned above, it was also observed that the larger the amount of the RT polar phase, the faster the reaction up to a certain point. A similar relationship between the maximum pressure drop rate (representing the reaction rate) and the absolute amount of catalyst in the mini-reactor was also observed.

It was also entirely unexpected to find out that the mole % selectivity to adipic acid did not change with wt % RT polar phase present or with the amount of catalyst present. It remained substantially constant. The mole % selectivity to adipic acid is defined as the moles of adipic acid formed in the reaction, multiplied by 100, and divided by the sum of moles formed of adipic, glutaric and succinic acids.

It was also found that, within the limits examined, the selectivity to adipic acid was independent of the amount of acetaldehyde present or the molar ratio of acetaldehyde to cobalt(II) acetate.

Regarding the RT and other temperature polar and non-polar phases, it should be pointed out that their compositions may vary considerably depending on the amount and nature of catalyst, water, solvent, hydrocarbon, initiator, etc. Thus different conclusions stated hereinbelow are relative to polar and non-polar phases made as described in each particular case. However, a person of ordinary skill in the art, based on the teaching of this invention, may find desired relations of other polar and non polar phases in other occasions with only a minimal effort.

The implications of these finding have an enormous impact in a large number of aspects regarding the direct synthesis of adipic acid by oxidation of cyclohexane with oxygen. These findings indicate the following important process steps, among others, which may be performed to drastically improve and control the oxidation process. These steps may be performed individually or in any combination, depending on the circumstances, including but not limited to reactor design, reactor-peripherals' design, pre-existing or new-reactor, parameter limitations, etc.

(1) Since the reactivity shows a maximum at a range of about 65% RT polar phase (as made in composition iii of Table 2) and higher, especially without sacrificing selectivity, the reaction should be driven toward that range of RT polar phase (nevertheless, increase of total catalyst level with increase in RT polar phase should be kept in mind);

(2) Since the reactivity (the amount of reaction taking place in a given reaction volume) shows a similar behavior regarding catalyst level, especially without sacrificing selectivity, the reaction should be driven toward higher catalyst level, preferably under the precipitation point at which the catalyst starts precipitating;

(3) Since cyclohexane is the main contributor to the formation of the non-polar phase, the reaction should preferably be driven toward the minimum amount of cyclohexane in such a manner that there is always an adequate amount of cyclohexane in the liquid and vapor forms in order to avoid starvation of the reaction because of lack of cyclohexane; in all instances it is preferable- to be controlled below that amount which causes a second phase to form at reaction conditions; minimization of cyclohexane in the reactor has a very important additional beneficial effect, which is related to safety; in case of accidental ignition in the reactor, there will be considerably less fuel (cyclohexane) to promote an explosion;

(4) Since acetic acid is a main contributor to the formation of the polar phase, the reaction should be driven toward the maximum amount of acetic acid in such a manner that excessive dilution is avoided or prevented; this step should preferably be coordinated with step (3) so that the amount of acetic acid does not cause lowering of the amount of cyclohexane to cause in turn starvation of the reaction because of lack of cyclohexane; preferably, the amount of acetic acid used should be such as to produce a ratio of RT polar phase to RT non-polar phase in the range of over about 65% RT polar phase combined with an adequate amount of cyclohexane to avoid cyclohexane starvation of the reaction;

(5) In order to operate with a single-phase system, which is highly preferable for multiple reasons, the reaction should be maintained at a temperature equal to or higher than the phase-critical temperature (as defined earlier) within limits to ensure that selectivity and yield do not suffer unacceptably;

(6) Since water is a strong contributor to the formation of two phases from a single phase, which is undesirable, but since it is believed to help the hydrolysis of undesirable ester by-products formed during the reaction, and because it is also believed to increase yield and selectivity of adipic acid, its content in the reaction mixture should be driven toward the maximum amount of water which does not cause the formation of a two-phase system from the single phase at least at the reaction temperature, unless downstream separations become adversely affected in so doing.

(7) In order to avoid or prevent precipitation of catalyst at room or lower temperatures at which the adipic acid is crystallized, the amount of catalyst in the mixture should be driven toward a region below the precipitation point of the catalyst in the reacted and cooled mixture;

A preferred embodiment of this invention is illustrated in FIG. 1. In FIG. 1, there is depicted a device or continuous reactor system 10 comprising a reaction chamber 12. A recycle feeding or inlet line 14, a new raw material feeding or inlet line 16, a gaseous oxidant feeding or inlet line 18, a gas outlet line 19, a sampling line 20, a predominantly non-gaseous outlet line 21, and means for measuring temperature, such as thermocouples 22 and 24 for example, are connected to the reaction chamber 12. Other elements, commonly used with reaction chambers, such as pressure monitors and controllers for example, and the like, although preferably utilized according to the instant invention, are not shown in FIG. 1 for purposes of clarity. Also, optional means for conducting chemical analysis of the contents of the reaction chamber 12 are not shown also for purposes of clarity.

The sampling line 20 leads to a phase analyzer 26, which provides liquid phase information to a computerized controller 28 through input line 26'. An example of phase analyzer will be described at a later point. The optional means (not shown) for conducting chemical analysis of the contents of the reaction chamber 12, preferably, also provide ingredient content information to the computerized controller 28. The inlet, outlet, input or output lines may be positioned in any suitable location of the reaction chamber 12. The words "inlet" and "outlet" are used for lines which feed or withdraw materials, respectively, while the words "input" and "output" are used for lines which provide information to the computerized controller 28, or are utilized by the controller to control other elements of the device, respectively.

The predominantly non-gas outlet line 21 leads to a material management station 30, at which the products of reaction, any by-products, non-converted raw materials, etc., are separated by well known to the art techniques. Such techniques may involve filtration, distillation, crystallization, other types of separation, evaporation, cooling, heating, storage, decontamination, incineration, disposal, etc.

The desired product of reaction follows product path 32, the non-recyclable by-products follow non-recyclables path 34, while recyclable materials follow recyclables line 36, which line 36 leads to an analytical apparatus 38 for analysis of the contents of the recyclables. The analytical apparatus 38 samples the recyclables for analysis and allows the major portion of said recyclables to enter line 36ii. Line 36 may comprise one or a plurality of lines, depending of the nature of the recyclables. Some of these lines may even circumvent the analytical apparatus 38, if so desired (if for example the content of the recyclable material under consideration is known or previously determined by any of well known to the art techniques).

The recyclables follow line 36ii, which leads to a three way valve 39, in a manner that the recyclables may follow line 40 or 42 or both in any desired ratio. Line 42 leads back to the material management station 30 for storage or retention or rework, or the like, while line 40 leads to a first heat exchanger (including cooler or heater or the like) 44.

The 3 way valve 39 is controlled by the computerized controller 28 through output line 38". Similarly, the heat exchanger 44 is controlled by the computerized controller 28 through output line 44". Preferably one or more input lines (not shown for purposes of clarity) provide temperature information to the computerized controller 28 regarding the recyclables as they enter end exit the heat exchanger 44.

The recyclables enter the reaction chamber 12 after they pass through flowmeter 46, which gives recyclables flow data to the computerized controller 28 through input line 46'. Input lines 22' and 24' feed the computerized controller 28 with temperature information within the reaction chamber 28. Both lines may be necessary, or only one, or more than two, depending on the information required in each particular case.

Flow regulation valves 50, 52, 54, 56, and 58 are connected to inlet lines 50i, 52i, 54i, 56i, and 58i, which provide hydrocarbon, solvent, catalyst, promoter, and other adjuncts, respectively, to a pre-mixing vessel 48. The premixing vessel 48 is preferably of small size and positioned in a way that all its contents are moving out of it and through line 16, so that if more than one phase is present, there is no accumulation of a particular phase in the pre-mixing vessel. Pre-mixing vessel 48 is connected with a second heat exchanger (including cooler or heater or the like) 60, which in turn is connected to the reaction chamber 12. The inlet lines 50i, 52i, 54i, 56i, and 58i, may however be directly connected to the second heat exchanger 60 or to the reaction chamber 12.

Flow regulation valves 50, 52, 54, 56, and 58 are controlled by the computerized controller 28 through output lines 50", 52", 54", 56", and 58", respectively. A number of flowmeters (not shown for purposes of clarity) connected to lines 50i, 52i, 54i, 56i, and 58i, provide flow information regarding hydrocarbon, solvent, catalyst, promoter, and other adjuncts, to the computerized controller 28 through multiple input line 62.

The reaction chamber 12 may be heated or cooled by heating or cooling means (not shown) well known to the art.

The lines 14 and 16 may merge together into a single line (not shown), and feed the reaction chamber through said single line. The phase analyzer 26, or an additional phase analyzer (not shown) may also be connected to this single line, so that it detects the presence of a second phase qualitatively or quantitatively, even before the liquid enters the reaction chamber, and before the oxidation starts taking place. Preferably, the determination of the second phase takes place under the same temperature and pressure of the reaction (if the pressure is not excessive). One example of the phase analyzer 26 is better illustrated in FIG. 2. It may comprise an at least partially transparent cell 62 for accepting liquid from the reaction chamber 12, and a detector 66 adapted to move up and down the height of the cell 62, in order to detect the presence of more than one liquid phases 64. The nature of the cell 62 is preferably such as to accept high pressures, preferably similar to the reaction pressures. The detector 66 can be a color detector, a refractive index detector, an ultrasonic detector, or in general, any type of detector that can distinguish and differentiate between liquids by using a property of the two liquids, which property may differentiate one from the other.

Figure 3:
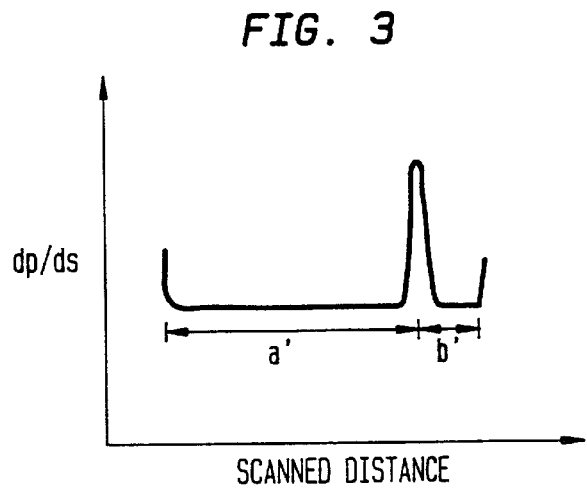
FIG. 3 illustrates the response of the phase analyzer of FIG. 2, when the detector scans the analyzer's cell, which contains two liquid phases.

If the phases separate to a lower phase having a height "a", and to an upper phase having a height "b", the differential of the detected property per scanned distance $dp/ds$ ("p" being the property, such as color for example, and "s" being the scanning distance as shown by the arrows A) will give a graph as shown in FIG. 3, wherein a'/b'=a/b, from which the degree of second phase formation may be determined.

If the phases are difficult to separate into distinct portions, additional techniques to aid such separation may be utilized. Centrifuging, ultra-centrifuging, addition of flocculation agents, and the like, are example of such techniques.

Figure 2:
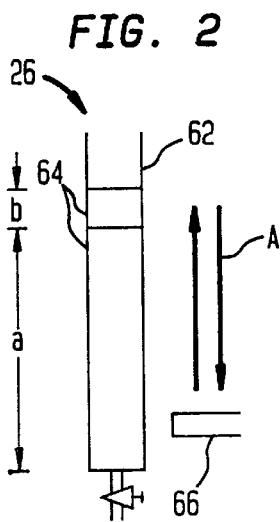
FIG. 2 illustrates schematically a phase analyzer, which may be utilized according to the present invention.

Although in FIG. 2 the detector 66 is shown to reside outside the cell, it may very well reside inside the cell 62. A conductivity detector is an example of a detector that should come in contact with the liquid phases and preferably be inside the cell.

The detector may be a single detector traveling up and down the height of the cell, or otherwise scanning the cell, or it may be two or more detectors located steady at different positions of the cell. In the case of using two detectors, it is preferable to arrange one detector in the vicinity of the bottom of the cell and one detector in the vicinity of the top of the cell. It is obvious that in the case of relative movement of the detector with respect to the cell, the cell may be the moving element and the detector the steady element. Instead of utilizing a detector, an observer may visually detect the levels of the two liquids and provide this information to the computerized controller 28.

The phase detector may also be based on measuring or detecting the turbidity (cloudiness) of the mixture of one phase dispersed in the other phase, since the two phases, for all practical purposes and substantially always, will have different indices of refraction. A single liquid phase will be clear, but a second phase dispersed in another phase will produce a turbid mixture. Care will have to be taken in this case to filter out any solid matter before determination of the turbidity. Light scattering may also be used for detection of a finely emulsified second liquid phase into a first liquid phase. The temperature at which the cell 62 and its contents are subjected to, may be ambient temperature in the range of 20 to 25° C., any other temperature, or preferably the same temperature as the first temperature, which is the reaction temperature in the reaction chamber 12 in a zone that the reaction occurs (reaction zone). Depending on the temperature at which the cell 62 operates it may have to also be under pressurized conditions and closed to maintain its contents in the liquid state.

In operation of this embodiment (see FIG. 1), hydrocarbon, solvent, catalyst, promoter and any other desired adjuncts are added to the pre-mixing vessel 48, where they are mixed together. The pre-mixing vessel is small enough and positioned in a manner that if there is phase separation, no particular phase remains behind, but all phases are commingled and they proceed through the second heat exchanger 60 and to the reaction chamber 12 through line 16. The feed rates of the new raw materials fed through lines 50$i$, 52$i$, 54$i$, 56$i$, and 58$i$ depend on the feed rates of the recyclables fed to the reaction chamber 12 through recycle feeding line 14. Information regarding the analytical results from the analytical apparatus 38 is provided to the computerized controller 28, which combines this information with the information from the flowmeter 46 and the information from the flowmeters (not shown) of lines 50$i$, 52$i$, 54$i$, 56$i$, and 58$i$, and calculates the total feed rate of each individual ingredient entering the reaction chamber 12.

The computerized controller preferably gives precedence to the recyclables, and then it adjusts each of the valves 50, 52, 54, 56, and 58 through output lines 50", 52", 54", 56", and 58", respectively, in a manner that the total feed rate of each individual ingredient entering the reaction chamber 12 has a desired value. The desired value of each ingredient feed rate is preferably adjusted toward formation and maintenance of a single phase at the reaction temperature, otherwise called the first temperature.

Of course, when the operation starts, there are no recyclable materials, so that only new raw materials start entering the system through one or more of lines 50$i$, 52$i$, 54$i$, 56$i$, and 58$i$, and finally enter the reaction chamber 12 through line 16. During starting the operation, the different feed rates of new raw materials are arranged so that a single phase exists at the first temperature. As already mentioned earlier, when talking about a single or multiple phase in this description, the inventors mean single or multiple liquid phases. When the inventors want to refer to a solid phase, they specifically refer to a solid phase.

The balance of materials is also preferably arranged to be such that when water starts being formed during the oxidation, no second phase is formed. The amount of water formed depends on the conversion taking place when the system attains a steady state. The more solvent, acetic acid for example, is present at this steady state, the more water may be withstood by the system without formation of a second phase. Since the formation of water is substantially unavoidable when a hydrocarbon is oxidized, and in some respects its presence may even be desirable (for at least partial hydrolysis of undesirable ester by-products, for example), it is preferable to work at a steady state which can contain at least a predetermined content of water without the formation of a second phase. Removal of water in any step of the process, if necessary or desired, may be achieved by a number of ways, including for example distillation, addition of acid anhydrides, and other well known to the art methods.

The more hydrocarbon, cyclohexane for example, is present in the reaction chamber the higher the potential of formation of a second phase. At the same time, if too little hydrocarbon is present, the reaction starts starving from lack of hydrocarbon. According to the instant invention, the amount of hydrocarbon present in the steady state is preferably just above the point at which starvation is observed. "Just above" starvation means preferably between 0 to 20% above starvation, and more preferably 5 to 20% above starvation.

At the same time that the above mentioned ingredients enter the reaction chamber 12, a gas containing an oxidant, preferably oxygen, enters the reaction chamber through the gaseous oxidant feeding line 18, and it comes in contact with the mixture containing the hydrocarbon.

The reaction temperature or first temperature is monitored by one or more thermocouples, such as thermocouples 22 and 24, for example, which provide temperature information to the controller 28.

The computerized controller 28, based on this temperature information adjusts the first and second heat exchangers through output lines 44" and 60", respectively, in a manner that in combination with the heat released by the reaction, and the thermal characteristics of the reaction chamber 12, the first temperature attains and maintains a desired value. In order to lower the temperature in the reaction chamber, the heat exchangers are adjusted to lower the temperatures in lines 14 and 16. In addition to or instead of this, the reaction chamber itself may be provided with heating and/or cooling means (not shown for purposes of clarity, but well known to the art), controlled by the computerized controller 28, so that the temperature attains and maintains the desired value. The desired value may, of course, be a desired range of values.

As the reaction or first temperature is raised, the potential for formation of a single phase is increased, and the rate of reaction is increased. However, the selectivity to the desired final product may suffer. Therefore, a balance among rate of reaction, selectivity, and reaction temperature (first temperature) has to be decided. This decision may depend on the particular circumstances, and may be based on economical, safety, environmental, and other considerations.

Thus, the temperature may be adjusted through the computerized controller 28 within the desired range in a manner to promote the formation and/or maintenance of a single phase. If a single phase already exists, the temperature may preferably be reduced to the minimum limit of the desired range, and maintained there, if this decrease in temperature does not cause the formation of a second phase.

Lowering the pressure within the reaction chamber 12 moves the system toward a single phase formation since more hydrocarbon, cyclohexane for example, evaporates and the content of hydrocarbon in the liquid decreases. If inert gases are present in the gaseous oxidant (if the gaseous oxidant is predominantly a mixture of oxygen and nitrogen, for example), it is preferable that the partial pressure of oxidant, oxygen for example, is maintained constant during lowering the total pressure.

Increasing gas sparging in the case of a stirred-tank reaction chamber, or in general the flow of the gaseous oxidant in the case of an atomization reactor (described for example in our aforementioned patent and patent applications) has a similar effect as lowering the pressure.

Lowering the conversion, or hold-up time in the reaction chamber 12, decreases the amount of water formed, which has as an effect to promote the formation of a single phase. Lower conversion decreases the amount of acid formed, predominantly adipic acid for example, in the oxidation of cyclohexane, which has little or no effect on second phase formation. Lower conversion also increases the amount of unreacted hydrocarbon, cyclohexane for example, present in the reaction zone, which promotes the formation of two liquid phases, but this effect is rather small as compared to the stronger effect of water. The net result is believed to be that lower conversion promotes formation of a single liquid phase.

Lowering the amount of catalyst, cobalt(II) acetate tetrahydrate for example, also promotes the formation of a single phase. It should be noted here that when cobalt(II) tetrahydrate is used, water is necessarily introduced, corresponding to the water of hydration of the cobaltous acetate salt.

If the formation of a second phase is detected by the phase detector 26, the detector 26 transfers such information to the computerized controller 28 through input line 26'. The computerized controller 28 in turn takes steps toward reformation again of a single phase in the reaction chamber 12, by ordering one or more of the elements that it controls to function in a manner directed toward the reformation of the single phase, as described above. Although, depending on the particular circumstances, the functioning or activation of the miscellaneous elements controlled by the computerized controller 28 may be arranged in any desired precedence order, it is preferable in most occasions, according to the present invention, to be arranged as follows:

For stirred-tank reactors, when formation of a second phase is detected at the same temperature as the temperature prevailing in the reaction zone, the computerized controller gives precedence to decreasing the feed rate of the hydrocarbon by stepwise closing valve 50 through output line 50". The steps are preferably between 1 to 60% of the feed rate at the time that the formation of the second phase was detected, more preferably 1 to 30%, and even more preferably 2 to 10%. At a predetermined time (preferably ½ to 10 minutes, and more preferably 1 to 2 minutes) after each step, a sample is taken again through line 20 to the phase analyzer, where it is examined, and the results are provided to the computerized controller 28. If a single phase has been reformed, no further action is taken. If a single phase has not been formed the same process may be repeated.

If for some reason water is fed to the system through line 58i, the computerized controller 28 gives second precedence to valve 58 through output line 58", and a similar procedure as above is followed. This step, however, may assume first precedence in case that the amount of cyclohexane fed to the reaction chamber 12 moves below a point at which the reaction starts starving because of lack of adequate hydrocarbon, such as cyclohexane for example.

Figure 4:
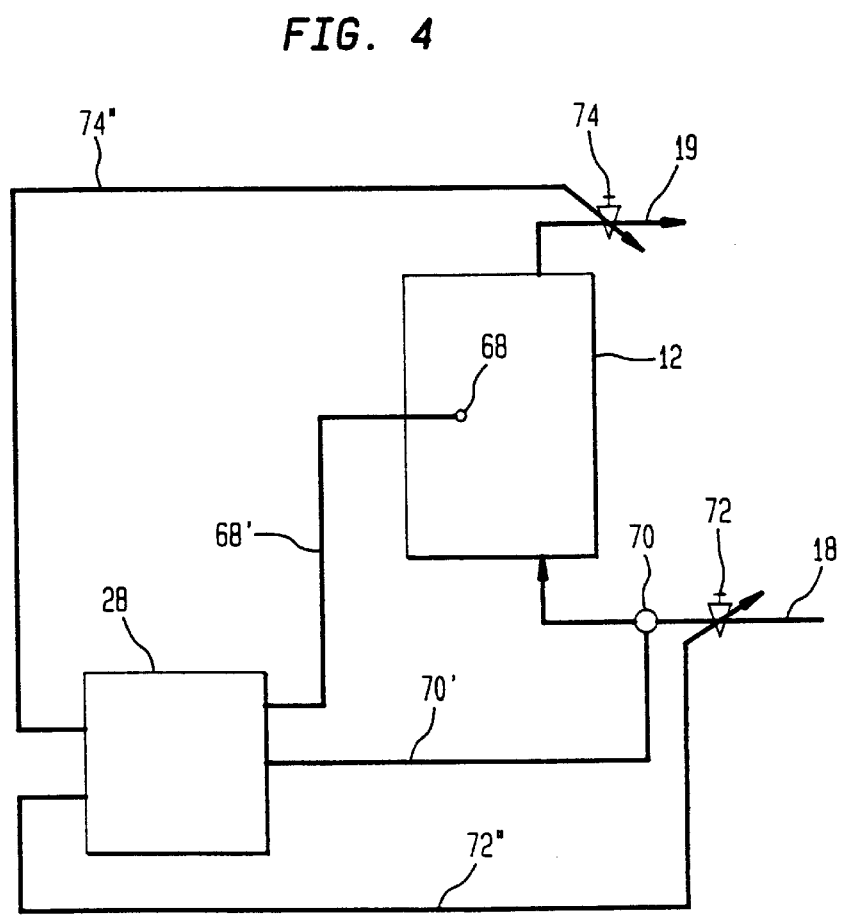
FIG. 4 shows the elements related to the pressure and the gaseous oxidant flow rate controls.

The next or third precedence is given to the rate of gaseous oxidant flow through line 18, which is also regulated (not shown in FIG. 1 for purposes of clarity) by the computerized controller 28, as better shown in FIG. 4, wherein the majority of the elements is not shown. FIG. 4 shows the elements related to the pressure and the gaseous oxidant flow rate controls. The reaction chamber 12 is provided with a pressure monitor 68, which transmits pressure information to the computerized controller 28 through input line 68'. The gaseous oxidant feeding line is provided with a flowmeter 70, which provides flow rate information to the computerized controller 12 through input line 70'. The computerized controller 28 controls valve 72 on the gaseous oxidant feeding line and valve 74 on the gas outlet line 19 through output lines 72" and 74".

If the above described steps are not adequate to eliminate the second phase, and provide a single phase, the computerized controller 28 opens the valve 72 in a manner that the flow increases stepwise from the value that it had to a higher value, which causes removal of hydrocarbon and water. The steps or increments of increase are preferably between 1 to 60% of the feed rate at the time that the formation of the second phase was detected, more preferably 1 to 30%, and even more preferably 2 to 10%. As in the previous cases, a predetermined time (preferably ½ to 10 minutes, and more preferably 1 to 2 minutes) after each step, a sample is taken again through line 20 to the phase analyzer, where it is examined, and the results are provided to the computerized controller 28. If a single phase has been reformed, no further action is taken. If a single phase has not been formed the same process may be repeated. In order to keep the pressure within the reaction chamber constant, valve 74 is also opened accordingly, so that the pressure as detected by the pressure monitor 68 does not increase.

The next or fourth precedence is given to pressure within the reaction chamber 12. If the above described steps are not adequate to eliminate the second phase, and provide a single phase, the computerized controller 28 closes further the valve 72 and opens further the valve 74 in a manner that the pressure decreases stepwise from the value that it had to a lower value. The steps or increments of pressure decrease are preferably between 5 to 30% of the pressure at the time that the formation of the second phase was detected, more preferably 5 to 20%, and even more preferably 10 to 20%. As in the previous cases, a predetermined time (preferably ½ to 10 minutes, and more preferably 1 to 2 minutes) after each step, a sample is taken again through line 20 to the phase analyzer, where it is examined, and the results are provided to the computerized controller 28. If a single phase has been reformed, no further action is taken. If a single phase has not been formed the same process is repeated. In order to keep the partial pressure of the oxidant constant, which is a preferred mode of operation, oxidant, such as oxygen for example, may be added through an additional port (not shown).

The computerized controller gives fifth precedence to increasing the feed rate of the solvent, acetic acid for example, by stepwise opening further valve 52 through output line 52". The steps are preferably between 1 to 60% of the initial feed rate, more preferably 1 to 30%, and even more preferably 2 to 10%. A predetermined time (preferably ½ to 10 minutes, and more preferably 1 to 2 minutes) after each step, a sample is taken again through line 20 to the phase analyzer, where it is examined, and the results are provided to the computerized controller 28. If a single phase has been reformed, no further action is taken. If a single phase has not been formed the same process may be repeated.

The computerized controller gives sixth precedence to decreasing conversion or increasing the feed rate of all entering raw materials, excluding catalyst, and the rate of the outgoing products through the predominantly non-gas outlet line 21, all in a proportional manner. This increase is conducted stepwise by further opening all involved valves, in a manner to increase all feeds and outgoing product flows proportionally to each other. The steps are preferably as in other cases between 1 to 60% of the initial feed rates and outgoing flows, more preferably 1 to 30%, and even more preferably 2 to 10%. A predetermined time (preferably ½ to 10 minutes, and more preferably 1 to 2 minutes) after each step, a sample is taken again through line 20 to the phase analyzer, where it is examined, and the results are provided to the computerized controller 28. If a single phase has been reformed, no further action is taken. If a single phase has not been formed the same process may be repeated.

Seventh precedence is given to the temperature, with increases allowed only within a predetermined region as described earlier.

Eighth precedence is given to decreasing the feed rate of catalyst.

In the above description of precedence for attaining and maintaining a single phase within the reaction zone, mention was made only to the valves for introducing new raw materials. It should be understood, however, that this would be preferably conducted in combination with the control of the recyclables from information received from the analytical apparatus 38 through input line 38', and from the flowmeter 46, by adjusting flow through valve 39 and the temperature through heat exchanger 44.

In the case of atomization reactors, temperature control for attaining and maintaining a single phase would take at least third precedence.

It should also be pointed out that a combination from different preference levels may be utilized before a multi-step process at each level of precedence. For example, the computerized controller may be programmed to perform only one step or a predetermined number of steps in each precedence level, the number of steps being the same or different at each particular level. Also, the computerized controller may be programmed to change the precedence levels, depending on any particular circumstances.

A preferable type of computerized controller comprises a "learning computer" or a "neuro-computer", the functionality of which is known to the art, and which collects information from different places of the device (for example pressure, temperature, chemical or other analysis, etc.), stores this information along with the result (reaction rate, for example), and it is programmed to use this information in the future, along with other data if applicable, to make decisions regarding the action to be taken (for example regarding precedence, steps within precedence, etc.) at each instance.

Although the miscellaneous functions are preferably controlled by the computerized controller 28, it is possible, according to this invention, to utilize manual controls for controlling one or more functions.

If the phase analyzer is at ambient temperature, correlations can be made between the analytical results and the ratio of RT polar phase to RT non-polar phase. If the ratio is small with substantially all catalyst in the RT polar phase, solvent should be added in adequate amounts to a ratio of solvent to hydrocarbon of preferably higher than 0.5, and more preferably between 0.5 and 1 at water levels preferably lower than 5%. All ratios in this discussion are by weight, unless otherwise stated.

As aforementioned, the methods of the instant invention may also comprise a step of correlating phase diagram data with variables selected from a group consisting of temperature in the reaction zone, pressure in the reaction zone, rate of gaseous oxidant flow, water feed rate, catalyst feed rate, hydrocarbon feed rate, solvent feed rate, and a combination thereof, in order to control the oxidation of the hydrocarbon by preferably controlling in the reaction zone a variable selected from a group consisting of temperature in the reaction zone, pressure in the reaction zone, rate of gaseous oxidant flow, water feed rate, catalyst feed rate, hydrocarbon feed rate, solvent feed rate, and a combination thereof.

Figure 5:
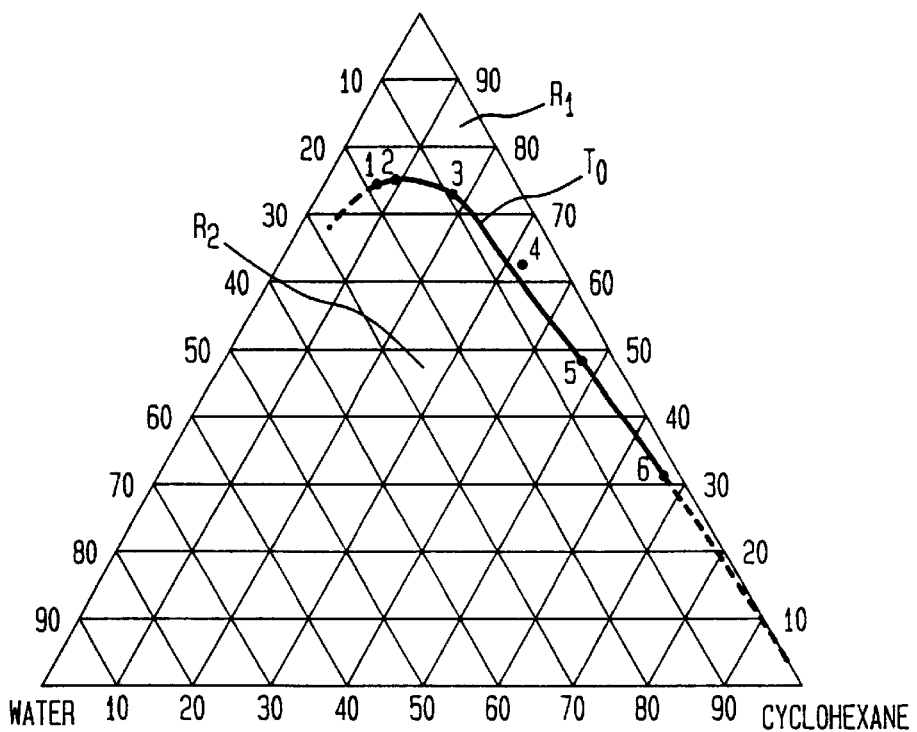
FIG. 5 shows a ternary phase diagram of (Acetic Acid)/(Cyclohexane)/(Water) at 100° C. at 0% level of cobalt(II) acetate tetrahydrate.
Figure 6:
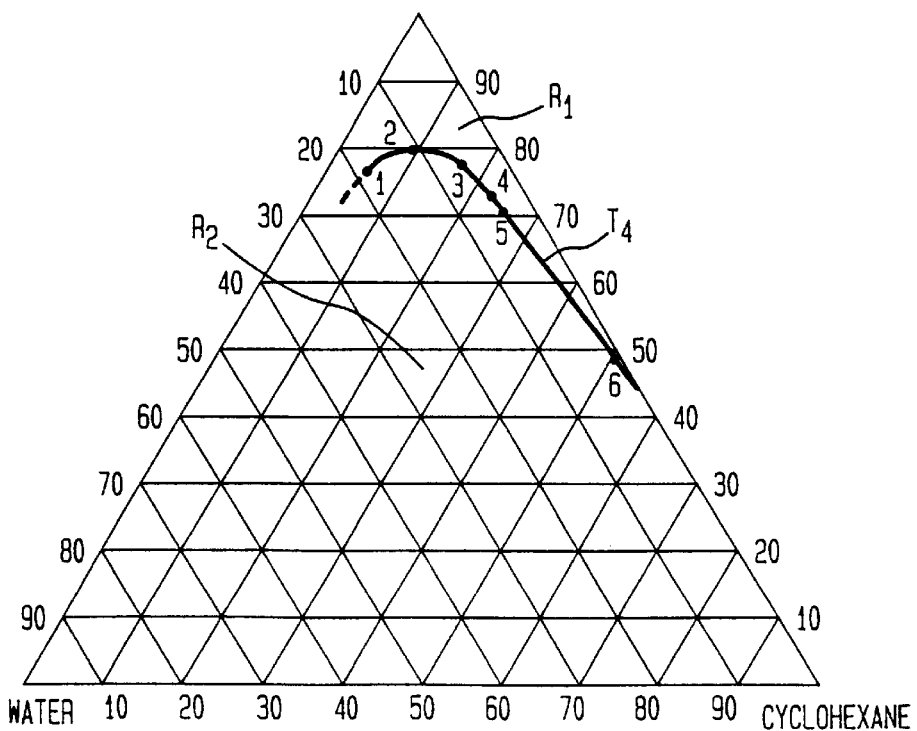
FIG. 6 shows a ternary phase diagram of (Acetic Acid)/(Cyclohexane)/(Water) at 100° C. at 4% level of cobalt(II) acetate tetrahydrate.

An example of such a ternary phase diagram of (Acetic Acid)/(Cyclohexane)/(Water) at 100° C., at a catalyst level of 0%, is shown in FIG. 5, wherein the one phase $R_1$ and two phase $R_2$ regions are separated by the transition line $T_0$. The one phase region $R_1$ is above the transition line $T_0$, while the two phase region $R_2$ is under the transition line $T_0$. Another example of such a ternary phase diagram of (Acetic Acid)/(Cyclohexane)/(Water) at 100° C., at a level of 4% catalyst is shown in FIG. 6, wherein the one phase $R_1$ and two phase $R_2$ regions are separated by the transition line $T_4$. The one phase region $R_1$ is above the transition line $T_4$, while the two phase region $R_2$ is under the transition line $T_4$.

As it can be seen, the presence of catalyst, cobalt(II) acetate tetrahydrate in this case, suppresses the one phase region to a certain degree. Presence of adipic acid in the mixture of components does not substantially move the transition curve. Ternary diagrams for different levels of catalyst, temperature, and/or other components, which may have influence on the transition curves may be created very easily, preferably experimentally. Thermodynamic data bases and computer flow-sheet simulation programs, for example, may be used as guidelines to determine the approximate position of the transition curve, which can then be refined and defined more accurately by limited experimentation. One easy way to construct an experimental ternary diagram for a given catalyst level, temperature, etc., is for example, to select different positions in the one phase region of the theoretical diagram close to the theoretical transition curve, and start adding water until a second phase is formed. This will define an experimental point on the experimental transition curve for the given catalyst level, temperature, etc. The exact compositions of the different experimental points in the diagrams shown in FIGS. 5 and 6 are listed in Tables 4 and 5, respectively. Points to the left of point 1 are omitted because the amount of cyclohexane involved is too small for most practical purposes. In Table 5, "*" indicates that the crystalline water of cobalt(II) acetate tetrahydrate is not included in the cited weight.

TABLE 4

COMPOSITIONS DEFINING TRANSITION CURVE $T_0$ IN FIG. 5
Experimental Data (0% Catalyst)

| Components | | Amount (grams) | wt % | | Amount (grams) | wt % |
|---|---|---|---|---|---|---|
| Acetic Acid | 1 | 15.105 | 75.70 | 2 | 15.586 | 77.93 |
| Water | | 3.750 | 18.79 | | 2.646 | 13.23 |
| Cyclohexane | | 1.099 | 5.51 | | 1.768 | 8.84 |
| Total | | 19.954 | | | 20.000 | |
| Acetic Acid | 3 | 15.124 | 75.27 | 4 | 12.005 | 62.18 |
| Water | | 1.762 | 8.77 | | 0.895 | 4.64 |
| Cyclohexane | | 3.207 | 15.96 | | 6.408 | 33.19 |
| Total | | 20.093 | | | 19.308 | |
| Acetic Acid | 5 | 9.859 | 48.30 | 6 | 6.550 | 32.75 |
| Water | | 0.537 | 2.63 | | 0.140 | 0.70 |
| Cyclohexane | | 10.018 | 49.08 | | 13.310 | 66.55 |
| Total | | 20.411 | | | 20.000 | |

TABLE 5

COMPOSITIONS DEFINING TRANSITION CURVE $T_4$ IN FIG. 6

| | Components | With 4 wt % Catalyst | | Catalyst free basis | |
|---|---|---|---|---|---|
| | | Amount (grams) | wt % | Amount (grams) | wt % |
| 1 | Acetic Acid | 15.198 | 72.88 | 15.198 | 75.95 |
| | Cyclohexane | 1.000 | 4.80 | 1.000 | 5.00 |
| | Catalyst | 0.844 | 4.05 | 0.000 | 0.00 |
| | Water* | 3.812 | 18.28 | 3.812 | 19.05 |
| | Total | 20.854 | | 20.010 | |
| 2 | Acetic Acid | 17.000 | 76.08 | 17.000 | 79.07 |
| | Cyclohexane | 2.000 | 8.95 | 2.000 | 9.30 |
| | Catalyst | 0.844 | 3.78 | 0.000 | 0.00 |
| | Water* | 2.500 | 11.19 | 2.500 | 11.63 |
| | Total | 22.344 | | 21.500 | |
| 3 | Acetic Acid | 14.762 | 72.56 | 14.762 | 77.08 |
| | Cyclohexane | 3.129 | 15.38 | 3.129 | 16.34 |
| | Catalyst | 0.812 | 3.99 | 0.000 | 0.00 |
| | Water* | 1.261 | 6.20 | 1.261 | 6.59 |
| | Total | 20.344 | | 19.152 | |
| 4 | Acetic Acid | 12.603 | 69.46 | 12.603 | 72.66 |
| | Cyclohexane | 3.843 | 21.18 | 3.843 | 22.16 |
| | Catalyst | 0.799 | 4.40 | 0.000 | 0.00 |
| | Water* | 0.899 | 4.95 | 0.899 | 5.18 |
| | Total | 18.144 | | 17.345 | |
| 5 | Acetic Acid | 13.606 | 67.68 | 13.606 | 70.48 |
| | Cyclohexane | 4.807 | 23.91 | 4.807 | 24.90 |
| | Catalyst | 0.798 | 3.97 | 0.000 | 0.00 |
| | Water | 0.893 | 4.44 | 0.893 | 4.63 |
| | Total | 20.104 | | 19.306 | |
| 6 | Acetic Acid | 9.799 | 47.25 | 9.799 | 49.22 |
| | Cyclohexane | 10.004 | 48.24 | 10.004 | 50.25 |
| | Catalyst | 0.831 | 4.01 | 0.000 | 0.00 |
| | Water* | 0.106 | 0.51 | 0.106 | 0.53 |
| | Total | 20.740 | | 19.909 | |

When such diagrams are used by the controller to operate the system and ensure that the reaction is conducted in one phase, analysis of the contents of the reaction chamber may be performed, preferably by Gas and Liquid Chromatography, and the flow rates of the different feeds (including recycled matter) may be changed accordingly to produce mixtures characterized by one phase. A similar procedure may be followed from diagrams produced at different temperatures, so that temperature manipulations may produce the desired results. Thus, for example, miscellaneous parameters may be changed to achieve the one phase desired condition, including but not limited to temperature in the reaction zone, pressure in the reaction zone, rate of gaseous oxidant flow, water feed rate, catalyst feed rate, hydrocarbon feed rate, solvent feed rate, and a combination thereof.

We have discovered that the unexpected combination of two critical phenomena is of utmost importance in the successful oxidation of a hydrocarbon, such as cyclohexane for example, to an acid, such as adipic acid for example.

The first of the two critical phenomena, as discussed above, is the formation of a second liquid phase during the time that the reaction is taking place.

If a second liquid phase is formed during the time that the reaction is taking place, the reaction rate drops to unacceptable levels, followed by unacceptably slow conversion rates, poor yields, and resulting in a totally uneconomical operation for all practical purposes.

The second of the two critical phenomena is catalyst precipitation during the time that the reaction is taking place. Catalyst precipitation during the time that the reaction is taking place has similar results as the formation of a second liquid phase. Even in a case that only partial precipitation of catalyst takes place, this precipitation results in catalyst deposition on different parts of the reactor system, plugging of pipes and valves, etc. Reaction rate and reactivity also suffer upon catalyst precipitation.

Thus, there is a severe problem in the state of the present art, when the reaction conditions permit either catalyst precipitation or formation of a second liquid phase.

We have found that under a given set of conditions, the amount of water in a liquid reaction mixture during a steady state oxidation of a hydrocarbon to a respective acid, has to be controlled within critical limits defined by the point of a second liquid phase formation and the point of catalyst precipitation. We have also found that under a given set of conditions, there is a minimum level of water under which the catalyst, cobalt(II) acetate tetrahydrate for example, precipitates, and over which the catalyst remains in solution. By the same token, we have found that there is a maximum level of water over which a second liquid phase is formed, and under which the substantially single-phase liquid is maintained. Therefore, for a given set of conditions, it is imperative that the water level, in a liquid mixture undergoing oxidation, is controlled between a maximum level of water over which maximum level the substantially single-phase liquid is transformed to two liquid phases, and a minimum level, under which minimum level, catalyst is precipitated. The problem becomes more severe as the catalyst, cobalt(II) acetate tetrahydrate for example, content increases, and also as the hydrocarbon, cyclohexane for example, content increases.

We also unexpectedly found that the catalyst, such as cobalt(II) acetate tetrahydrate or cobalt(II) 2-ethyl hexanoate for example, has a tendency to precipitate at higher temperatures.

This unexpected finding is extremely important because it may be used to detect a level of water at which the point of catalyst precipitation is being approached, and that additional water should be added to avoid catalyst precipitation, as will be described in detail hereinbelow.

Figure 7:
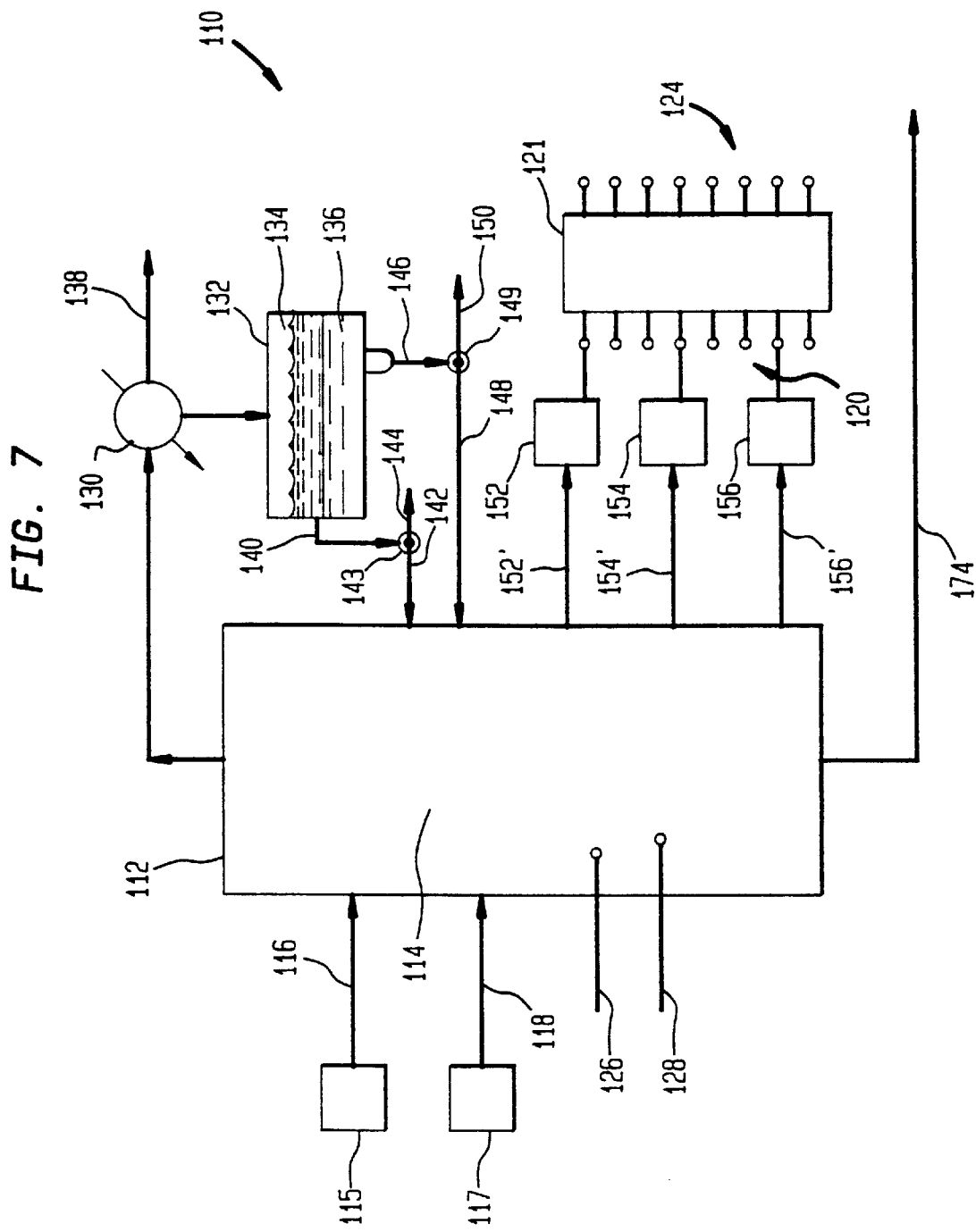
FIG. 7 illustrates a block diagram of another preferred embodiment of the present invention.

Referring now to FIG. 7, there is depicted a reactor system or device 110, comprising a reaction chamber 112 containing a reaction zone 114. The reactor system 110 is only partially shown for demonstrating the components necessary to exemplify the present invention. Miscellaneous treatment, product or by-product separation, recycling, etc. devices, well known to the art, are not shown for purposes of clarity and brevity.

The reaction chamber 112 encloses a reaction zone 114. Liquid feeding means 115 ending to a liquids feeding line 116 and gaseous feeding means 117 ending to an oxidant feeding line 118, are connected to the reaction chamber 112 for providing liquid feed and gaseous oxidant, respectively, to the reaction zone 114.

The reaction chamber 112 may be a stirred-tank reactor, atomization reactor, re-circulation reactor, or any other type of reactor, known to the art. The liquids feeding line 116 may be a single line or a multiple line. The liquid feeding means 115 may include heat exchangers, pre-mixing vessels, flowmeters, thermocouples, etc., and they are connected (not shown for purposes of clarity and brevity) to one or more of inputs 120 of a controller 122. In turn the controller 122 is connected to the liquid feeding means 115, through one of its outputs 124, and controls its operation by methods well known to the art.

In a similar manner, the gaseous feeding means 117 are connected (not shown for purposes of clarity and brevity) to one or more of inputs 120 of a controller 122. In turn the controller 122 is connected to the liquid gaseous oxidant means 117, through one of its outputs 124, and controls its operation by methods well known to the art.

Further, temperature monitor 126 and pressure monitor 128 are connected to the reaction chamber 112 for monitoring the temperature and the pressure in the reaction zone 114. They give relevant information to the controller 122 through input lines (not shown) connected to respective inputs 120 of the controller 122, so that the controller 122 adjusts the temperature and pressure of the reaction zone 114 in the reaction chamber 112, according to a predetermined way programmed in the controller 122, by well known to the art techniques.

A condenser 130 is also connected to the reaction chamber 112. One of the main purposes of the condenser 130 is to remove heat from the reaction zone 114. Vapors of condensibles, such as for example hydrocarbon, solvent, water, and the like may be refluxed directly to the reaction zone 114 of the reaction chamber 112, or they may be directed to a decanter 132, where they may be separated to an upper phase 134 and a lower phase 136. Off gases follow line 38 for preferably being scrubbed in order to remove escaping condensibles, and in turn they are usually freed to the atmosphere. Of course, in certain occasions, preferably before scrubbing, they are at least partially recycled to the reaction zone 114 of the reaction chamber 112. When recycled to the reaction zone, they may be introduced, partially or totally, under the liquid surface for supplemental sparging and/or reaction.

The decanter 132 is connected to line 140, which in turn communicates totally or partially with lines 142 and 144 through first valve 143. Thus, upper phase 134 liquids are partially or totally recycled to the reaction chamber 112, and/or partially or totally removed through line 144, usually for further treatment. The decanter 132 is also connected to line 146, which in turn communicates totally or partially with lines 148 and 150 through second valve 149. Thus, lower phase 136 liquids are partially or totally recycled to the reaction chamber 112, and/or partially or totally removed through line 150, usually for further treatment. The first valve 143 and the second valve 149 are preferably controlled by controller 122, so that desired feeding rates of each phase are either recycled to the reaction chamber 112 or they are directed for treatment and/or disposal.

Instead of the condenser 130 and the decanter 132, a distillation column (not shown) may be used for considerably better separation of the different condensible components, such as for example hydrocarbon, solvent, water, by-products, etc. Thus, the distillation column may be used in the same manner as the combination of the condenser and the decanter for both removing heat and for separation of the individual condensible components.

An analytical apparatus 152 is also connected to the reaction chamber 112 through line 152'. The analytical apparatus 152 is programmed by the controller 122 to take samples from the reaction chamber 112 and analyze them. This analytical apparatus preferably comprises HPLC and GC equipment, well known to the art, and it may be used to determine water, solvent, hydrocarbon, catalyst, oxidation products, oxidation by-products, etc. Of course, sampling of the contents of the reaction chamber 112 may be manual, with subsequent feeding to the analytical apparatus and then feeding the analysis results to the controller 122 for further processing.

In addition to or in place of the analytical apparatus 152 there is an upper water level monitor 154 (or 155) and a lower water level monitor 156 connected to the reaction chamber 112. Samples from the contents of the reaction chamber 112 are provided to the monitors 154 and 156 through lines 154' and 156', respectively. As above, this operation may also be manual and/or be based on visual observations, as it will be explained in more detail later. Further, the results from the two monitors 154 (or 155) and 156 may be fed automatically or manually to the controller 122. It is worth noting that the upper water level monitor 154 (or 155) may also serve as a more versatile monitor for detecting the level of hydrocarbon, and/or the level of catalyst, in addition to or instead of the level of water, at which level, a second liquid phase is formed. It may also serve to determine a higher second solvent level at or over which the substantially single-phase liquid is maintained or re-established in the reaction zone, despite rise in hydrocarbon level and/or catalyst level and/or water level, which rise would have resulted in formation of a second liquid phase if the solvent had remained at its initial level.

Figure 8:
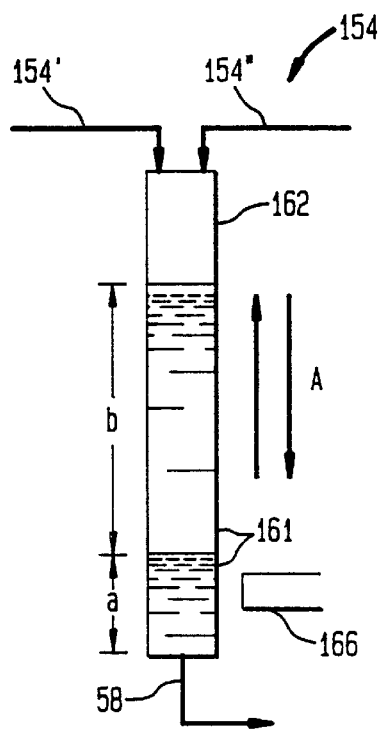
FIG. 8 illustrates schematically an upper water level monitor, which may be utilized in the embodiment of FIG. 7, and which may also be utilized for determining conditions for maintaining a substantially single liquid phase during oxidation of a hydrocarbon.

An example of an upper water level monitor 154 is better shown in FIG. 8. The upper limit water level monitor may comprise an at least partially transparent first cell 162 for accepting liquid from the reaction chamber 112 through line 154', and a first detector 166 adapted to move up and down the height of the first cell 162, in order to detect the presence of more than one liquid phases 164. The monitor 154 is also supplied with line 154", through which plain water or water from line 148 containing solvent, may be introduced to the monitor 154 in predetermined amounts (the amount of solvent is usually higher than the amount of water in the lower phase, and weight ratios of solvent to water of about 75 to 25 are within reality). An exit line 158 is used to remove the liquids from the first cell 162 after a determination has been made, and a new determination is due. The monitor 154 may also be provided with a mixing mechanism (not shown for purposes of clarity), which may be based on stirring, shaking, mixing, and any other techniques well known to the art. Vigorous mixing is preferred.

The nature of the first cell 162 of monitor 154 is preferably such as to accept high pressures, preferably similar to the reaction pressures. However, low pressures are also acceptable, as long as the contents (except for gases) of the cell do not substantially volatilize. For this purpose, it is highly preferable that the cell is as full as possible with sample during its operation, which will be discussed in detail later. The first detector 166 can be a color detector, a refractive index detector, an ultrasonic detector, or in general, any type of detector that can distinguish and differentiate between liquids by using a property of the two liquids, which property may differentiate one from the other.

Figure 9:
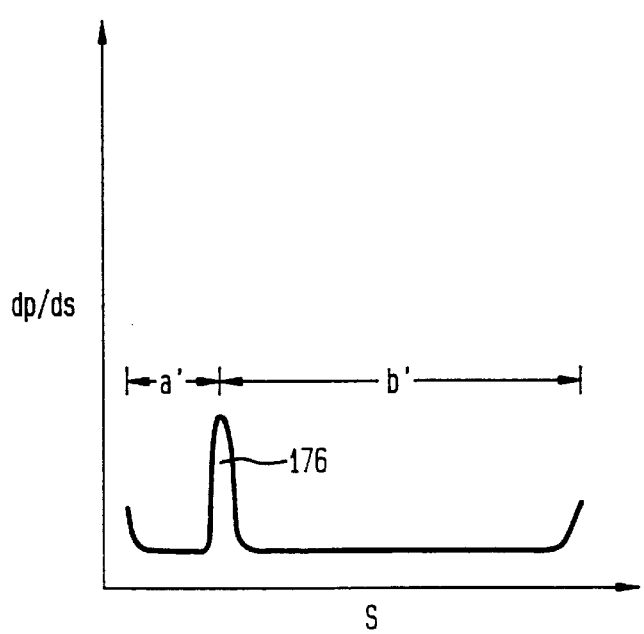
FIG. 9 illustrates the response of the phase analyzer of FIG. 8, when the detector scans the analyzer's cell, which contains two liquid phases.

If the phases 161 separate to a lower phase having a height "a", and to an upper phase having a height "b", the differential of the detected property per scanned distance dp/ds ("p" being the property, such as color for example, and "s" being the scanning distance as shown by the arrows A) will give a graph as shown in FIG. 9, wherein a'/b'=a/b, from which the creation or presence and the degree of second liquid phase formation may be determined.

If the phases are difficult to separate into distinct portions, additional techniques to aid such separation may be utilized. Centrifuging, ultra-centrifuging, addition of flocculation agents, and the like, are examples of such techniques.

Although in FIG. 8 the first detector 166 is shown to reside outside the first cell, it may very well reside inside the first cell 162. A conductivity detector is an example of a detector that should come in contact with the liquid and preferably be inside, and more preferably at the bottom of the first cell 162.

The first detector may be a single detector traveling up and down the height of the first cell, or otherwise scanning the first cell, or it may be two or more detectors located steady at different positions of the first cell. In the case of using two detectors, it is preferable to arrange one detector in the vicinity of the bottom of the first cell and one detector in the vicinity of the top of the first cell. It is obvious that in the case of relative movement of the detector with respect to the first cell, the first cell may be the moving element and the detector the steady element. Instead of utilizing a detector, an observer may visually detect the creation or presence and the levels of the two liquid phases and provide this information to the controller 122.

When two liquid phases are formed and are difficult to separate, the first detector 166 may also be based on measuring or detecting the turbidity (cloudiness) of the mixture, if one liquid phase is dispersed or emulsified in the other liquid phase, since the two phases, for all practical purposes and substantially always, will have different indices of refraction. A substantially single-phase liquid will be clear, but a second liquid phase dispersed or emulsified in the first liquid phase will produce a turbid mixture. Care will have to be taken in this case to filter out any solid matter before determination of the turbidity. Light scattering may also be used for detection of a finely emulsified second liquid phase in a first phase.

Figure 8A:
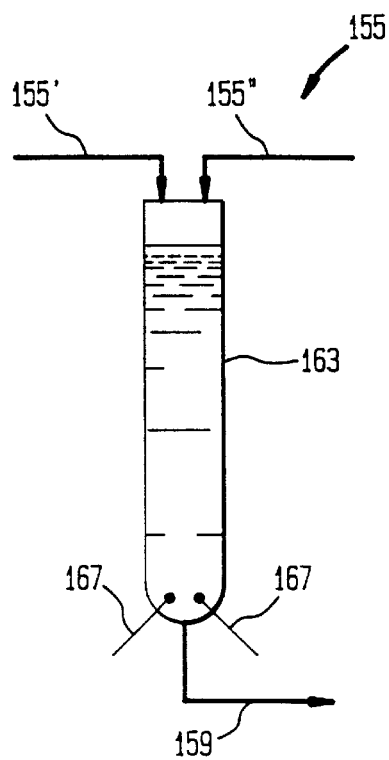
FIG. 8A illustrates schematically an upper water level monitor, based on conductivity measurements, which may be utilized in the embodiment of FIG. 1, and which may also be utilized for determining conditions for maintaining a substantially single liquid phase during oxidation of a hydrocarbon. The monitor is shown under conditions of a substantially single liquid phase.
Figure 8B:
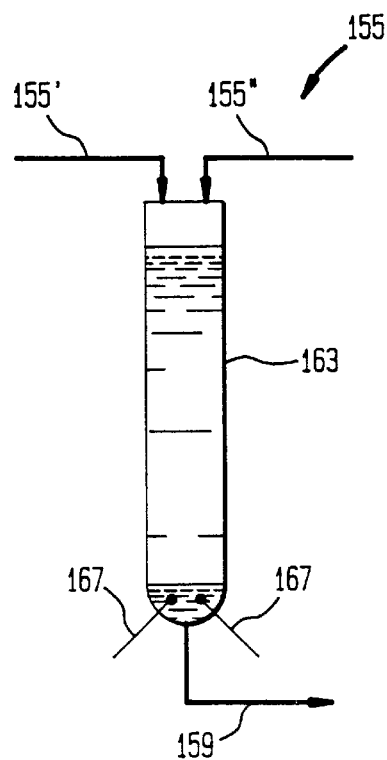
FIG. 8B illustrates schematically the same upper water level monitor, based on conductivity measurements, as shown in FIG. 8A under conditions of a second liquid phase formation.

Another example of an upper water level monitor 155, based on conductivity detection, is shown in FIGS. 8A and 8B, and comprises a cell 163 similar to cell 162 of monitor 154 (FIG. 8). In the vicinity of the bottom of cell 163, there are located conductivity leads, which measure conductivity, by well known to the art techniques. The cell 163 is also connected to a line 155' from which it may accept a sample from the reaction zone 114. It is further connected to line 155" through which water may be introduced. Of course, if appropriate, line 155" may be used for introduction of other liquids, such as for example hydrocarbon, catalyst, solvent, a mixture thereof, and the like. Line 159, connected to cell 163, is used as an exit line for the contents of cell 162, when they are not needed any further.

FIG. 8A shows one phase in the cell 163, while FIG. 8B shows a second liquid phase formation, which may be detected very easily by the conductivity probe 167, since the newly formed phase will have a highly different conductivity as compared to the one liquid phase system. Since the hydrocarbon, such as cyclohexane for example, with a small amount of dissolved solvent, is lighter than water with a large amount of dissolved solvent, such as acetic acid for example, the second liquid phase, which will be the polar phase, will reside at the bottom of the cell 163, and it will give a highly increased conductivity. Thus, it will be detected very easily. More conductivity probes may be placed at different positions of the cell to detect the ratio of the two phases if so desired. In a case where the second liquid phase is expected to take place in the vicinity of the top of the cell 163, the conductivity probe may be placed in an accordingly appropriate position.

Figure 10:
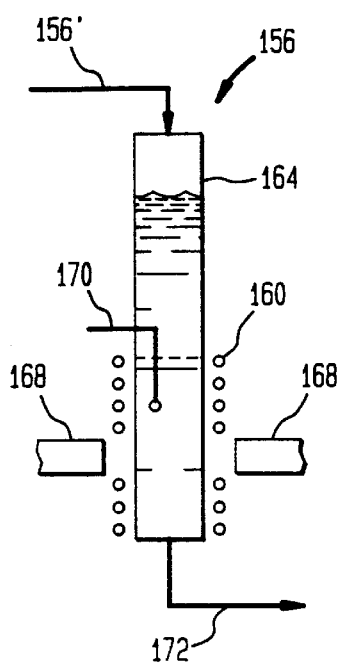
FIG. 10 illustrates schematically a lower water level monitor, which includes a second cell, before catalyst precipitation after a predetermined rise in temperature.
Figure 11:
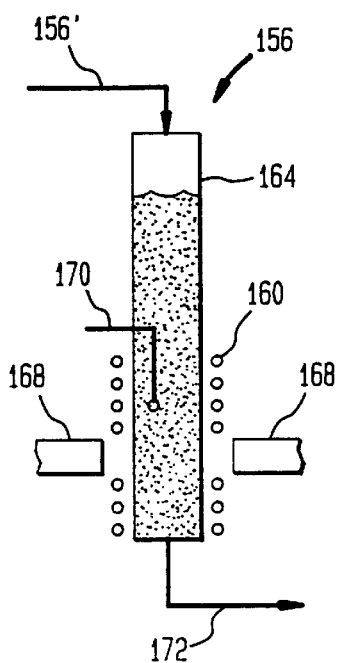
FIG. 11 illustrates schematically the same lower water level monitor of FIG. 10, after catalyst precipitation.

A low water level monitor 156, to detect catalyst precipitation, is better illustrated in FIGS. 10 and 11. Monitor 156 comprises an at least semitransparent, and preferably transparent, second cell 164, which is provided with heating means, such as a heating coil 160 for example, and a second detector 168, which is capable of measuring light (preferably visible in this particular case) absorption, or turbidity, and the like, through a medium. The second cell 164 is also provided with a thermocouple 170 for monitoring the temperature of the contents of the second cell 164.

The second cell 164 is connected to line 156' from which it is provided with liquid mixture from the reaction zone 114 of the reaction chamber 112. An exit line 172 is used to remove the liquids from the second cell 164 after a determination has been made, and a new determination is due. The monitor 156 is preferably provided with a mixing mechanism (not shown for purposes of clarity), which may be based on stirring, shaking, mixing, and any other techniques well known to the art.

The second cell 164 is preferably such as to accept elevated pressures and temperatures as the case is for the first cell 162.

The analytical apparatus 152, shown in FIG. 7, may comprise one or more devices or one or more sets of devices for analyzing not only the composition of the reaction zone 114, but also the composition of miscellaneous streams.

A liquid transfer line 174 is connected to the reaction chamber 112 for removing flowable matter from the reaction zone 114 for removal of oxidation product, such as adipic acid for example, further treatment for removal of undesirable by-products, recycling of other matter, etc.

In operation of this embodiment, hydrocarbon, such as cyclohexane for example, solvent, such as acetic acid for example, catalyst, such as cobalt acetate tetrahydrate for example, and initiator such as cyclohexanone or acetaldehyde for example, are initially charged in the reaction zone 114 of the reaction chamber 112 through line 116. As mentioned earlier, line 116 may be a single line or a multiple line for introducing raw materials as a totality or as individual streams, or as combination of streams. A small amount of water (for example 0.2 to 2% by weight based on total charge, depending on individual circumstances) may also be added to the reaction zone 114. The raw materials may be introduced at reaction temperature, which reaction temperature in the case of preparation of adipic acid from cyclohexane is preferably in the range of 60 to 160° C., more preferably in the range of 80 to 120° C., and even more preferably in the range of 90 to 110° C. Alternatively, the raw materials may be introduced at a different temperature than the reaction temperature, preferably lower temperature, and then be brought to the reaction temperature by means of heating or cooling elements, accordingly, inside or outside the reaction chamber 112. In the case of a stirred-tank reactor, the reaction chamber is filled to a predetermined degree, preferably larger than half the capacity of the reaction chamber 112. In the case of an atomization reactor, preferably, a small charge at the bottom of the reaction chamber 112 is introduced, which is recirculated from upper levels of the reaction chamber 112 toward the bottom of the reaction chamber 112, in the form of a spray, as discussed in our aforementioned patents and applications dealing with atomization reactors. For purposes of simplicity, the following discussion will be predominantly directed to stirred-tank reactors.

The temperature is monitored by the temperature monitor 126, and the pressure by the pressure monitor 128. Temperature monitors, such as thermocouples for example, and pressure monitors, such as strain gauges, or coil gauges for example, are devices well known to the art. Information received from the temperature monitor 126 and the pressure monitor 128 is fed to the controller 122 through inputs 120. The monitor 122 adjusts in turn the temperature and the pressure in the reaction zone 114 in the reaction chamber 112 to stay within desired limits, by well known to the art techniques.

The pressure in the reaction zone 114 is preferably adjusted to be such that a large part of the hydrocarbon and of the solvent remain as liquids at the operation temperature. In the case of the direct oxidation of cyclohexane to adipic acid, pressures between 10 and 500 p.s.i.g. are preferable, although they may range from a few p.s.i.g. to thousands of p.s.i.g. under certain circumstances.

During charging the raw materials, or after the desired charge has been completed, a gaseous oxidant starts being introduced through the oxidant feeding line 118. The gaseous oxidant is preferably either oxygen, or a mixture of oxygen with a substantially inert gas, such as nitrogen, carbon dioxide, noble gas, and the like. The partial pressure of oxygen is preferably 10 to 500 p.s.i.g., although it may vary broadly outside this range, depending on the individual circumstances. The flow rate of the gaseous oxidant through line 118 is preferably adequately high in a manner to avoid oxidant starvation in the reaction zone 114.

As the gaseous oxidant is introduced, the hydrocarbon starts being oxidized, liberating heat. The liberated heat may be removed by one or more cooling means, such as cooling coils inside the reactor for example. However, it is highly preferable to remove the heat of reaction by evaporating condensible matter from the liquids in the reaction zone 114. Thus, hydrocarbon, cyclohexane for example, along with solvent, acetic acid for example, and water with minor amounts of other condensibles, formed during the oxidation process, are evaporated and condensed in the condenser 130. The condensed matter is then refluxed directly into the reaction zone 114, or more preferably is introduced to a decanter 132. In the decanter 132, the hydrocarbon with some solvent (and a minor amount of water) is separated in an upper liquid phase 134, and the water with a considerable amount of solvent, as aforementioned, and a minimal amount of hydrocarbon, is separated in a lower liquid phase 136. Non condensible gases (non-condensible in the condenser 130), such as some oxygen, nitrogen, carbon dioxide, and the like, carrying along some hydrocarbon, some solvent, some water, etc., leaves the system for further treatment and/or disposal. Nevertheless, at least partial gas recycling of non-condensible gases, sub-surface to the liquid mixture in the reaction chamber 112, may also take place, if so desired.

In the place of condenser 130 and decanter 132, a distillation column may be used, directly connected to the reaction chamber 112. With the distillation column, the individual components of the condensible matter may be separated very efficiently.

The upper phase is preferably recycled to the reaction zone 114, preferably in its totality via lines 140 and 142. However, all or part of the upper phase 134 may be removed through line 144 for further treatment. The flow rates through these lines is controlled by the first valve 143, which in turn is controlled by the controller 122, through outputs 124.

The lower phase 136, containing water with solvent, may be partially or totally recycled to the reaction chamber 112 through lines 146 and 148. It may also be removed totally or partially through line 150 for further treatment and/or disposal and or recycling to some stage of the system. The second valve 149, which controls the flow through lines 146, 148, and 150 is in turn controlled by controller 122 through inputs 124.

After the oxidation has reached a desired point of conversion of the hydrocarbon, as determined by the analytical apparatus 152, which samples the reaction zone 114 through line 152, a stream of flowable matter starts leaving the reaction zone 114 of the reaction chamber 112 through the flowable matter transfer line 174. The flow rate of the flowable matter leaving the reaction chamber 112 through line 174 is controlled by the controller 122 through outputs 124. A flow of replenishing matter enters the reaction zone 114 of the reaction chamber 112 through the liquids feeding line 116 to replenish materials consumed during the oxidation. The average flow rates of liquid matter, entering and exiting the reactor device 110, should be equal to each other volume-wise, so that the average volume of matter in the reaction chamber 112 remains substantially constant. The flowable matter leaving the reaction chamber 112 through line 174 is transferred to other stages of the reactor device 110 (not shown for purposes of clarity) for separation of the product of oxidation, such as adipic acid for example, recyclable matter, by-products, etc.

Equilibrium and a steady state are achieved as the oxidation proceeds and is controlled by controller 122. Keeping the rest of conditions substantially constant, the degree of conversion may be increased or decreased by decreasing or increasing respectively the flow rates through lines 116 and 174.

According to the present invention a steady state has to be maintained in the presence of a substantially single-phase liquid, in addition to other requirements. One way to achieve a substantially single liquid phase is to program the controller in a manner that it takes the information from the analytical apparatus, compares it with a phase diagram, as explained below, and causes changes which will ensure a substantially single-phase liquid in the contents of the reaction chamber 112.

The variables which are important for maintenance of a substantially single liquid phase may be selected, among others, from a group consisting of temperature in the reaction zone, pressure in the reaction zone, rate of gaseous oxidant flow, water feed rate, catalyst feed rate, hydrocarbon feed rate, solvent feed rate, and a combination thereof. Under steady state conditions, and substantially constant temperature in the reaction zone, pressure in the reaction zone, rate of gaseous oxidant flow, catalyst feed rate, hydrocarbon feed rate, and solvent feed rate, the water feed rate may be used and adjusted in a manner to ensure a substantially single-phase liquid. Under the above stated conditions, there is a maximum feed rate of water, over which a second liquid phase is produced. Thus, the water feed rate has to be lower than this maximum in order to ensure the presence of just one substantially single-phase liquid.

Although phase diagrams may be multi-dimensional, ternary diagrams, which correlate three components, may be also used, if all other parameters remain constant. Also for different sets of specific parameters, respective ternary phase diagrams may be used according to the present invention. Examples of such parameters may be temperature, catalyst level, etc.

Examples of such ternary phase diagrams, shown in FIGS. 5 and 6 have been discussed earlier.

In general, according to this invention, when such computer flow-sheet systems and/or diagrams and/or catalyst precipitation data, are used by the controller to operate the system and ensure that the reaction is conducted in one phase, analysis of the composition of the reaction chamber may be performed, as described above, and the flow rates of the different feeds (including recycled matter and/or operating pressure) may be changed accordingly to produce mixtures containing a substantially single-phase liquid. A similar procedure may be followed from diagrams produced at different temperatures, so that temperature manipulations may produce the desired results. Thus, for example, miscellaneous parameters may be changed to achieve the one phase desired condition, including but not limited to temperature in the reaction zone, pressure in the reaction zone, rate of gaseous oxidant flow, water feed rate, catalyst feed rate, hydrocarbon feed rate, solvent feed rate, and a combination thereof. However, if all the parameters are kept constant, then the water feed rate becomes the critical parameter for ensuring one substantially single liquid phase. The water is preferably initially provided from the decanter 132, and secondarily by addition of non-recycled water, through line 116 for example.

In order to determine the maximum amount of water allowed in the reaction zone 114, or the maximum flow rate of water entering the reaction zone 114, a different technique than the one described above may also be used. According to this technique, the upper water level monitor is utilized. As aforementioned, a sample of the contents of the reaction zone 114 of the reaction chamber 112 is transferred to the first cell 162 (FIG. 8) through line 154'. Preferably the sample fills the major part of the first cell, so that there is only a small free space above the liquid. This is important because only limited amounts of vapors may occupy the small space, thus preventing alteration of the composition of the underlying sample. The temperature of the sample in the first cell 162 is preferably maintained the same as the temperature within the reaction zone 114. Since the equilibrium steady state in the reaction zone 114 has been selected such as to contain only a substantially single liquid phase (regardless of the existence or not of solid or gaseous phases), the sample in the first cell 162 also contains a substantially single-phase liquid. However, if for any reason at all, two phases are observed in the sample of the first reaction zone 114 contained in the first cell 162, the flow rate of water to the reaction zone 114 is stepwise decreased until a sample taken from the reaction zone indicates existence of only a substantially single liquid phase. As aforementioned, the source of water is preferably the decanter 132, and only if the decanter 132 cannot provide adequate amounts of water to the reaction zone 114, a different or additional supply of water may be used.

Nominally, in an example concerning the case of a Plant which makes about 200 million pounds of adipic acid per year, with a cyclohexane feed of about 40%, a catalyst (cobalt(II) acetate tetrahydrate) feed of about 0.5 to 1%, and a cyclohexane conversion to dibasic acids (adipic, glutaric, and succinic) of about 30%, a water feed of about 1% (in addition to the crystalline water of the cobalt(II) acetate tetrahydrate), a reaction zone pressure of 40 p.s.i.a., a 4/1 recycled gas to purged gas ratio, the water (in excess to the crystalline water of the cobalt(II) acetate tetrahydrate) in the reaction zone 114 may vary roughly from about 0.5% at 0% recycle of the lower phase in the decanter 132 to about 4% by weight at full recycle of the lower phase in the decanter 132. Water content in the reaction zone 114 rises moderately with increasing recycle of the lower phase until about 70–80% recycle, at which point water content in the reaction zone 14 starts to sharply rise with further increases in lower phase condensate recycle. Although the water in the feed is 1%, a high enough amount of water evaporates azeotropically with cyclohexane to bring the water level in the reaction zone 114 to a level of about 0.5%, when no recycled water is used. If no water at all (recycled or not) is fed to the reaction chamber 112, the level of water (in addition to the crystalline water of the cobalt(II) acetate tetrahydrate) in the reaction zone 114 is dropped to about 0.2 to 0.3% by weight.

The first detector 166, moving up and down in the direction of arrows A may detect a second liquid phase as described earlier, and as shown in FIG. 9. Initially, since a substantially single liquid phase only exists, no peak, such as peak 176 is present in the graph of FIG. 9. At this point, a small amount of water is added to the contents of the first cell 162 through line 154". The added water may be coming either from the lower phase 136 of the decanter 132, containing considerable amounts of solvent, or as substantially pure water. The contents of the first cell 162 are preferably maintained at substantially the same temperature as the operation temperature in the reaction zone 114.

In sequence, the contents of the first cell 162 are thoroughly mixed with the added water, preferably by vigorous mixing or shaking the first cell 162. After each increment of water has been added and mixed, the first cell 162 is allowed to stand still for a short period of time, preferably ½ to 1 minute. The first detector 166 scans then the first cell 162, as described above, to determine whether a second liquid phase has been formed. If the first detector 166 does not detect the formation of a second liquid phase, a new small portion of water (preferably having the lower phase 136 of the decanter 132 as source) is added to the cell 162 through line 154". The contents of the first cell 162 are again thoroughly mixed with the added water, preferably by vigorous mixing or shaking, the first cell 162. The first detector 166 scans again the first cell 162, as described above, to determine whether a second liquid phase has been formed. This procedure is repeated until a second liquid phase is detected by the presence of a peak, such as peak 176 in the graph of FIG. 9. At this point, the total amount of water (calculated as the % water by weight) present in the composition of the first cell 162, at the operation temperature, represents the maximum water level in the cell, and in the reaction zone 114 for all practical purposes, at which and over which the substantially single liquid phase is transformed to two liquid phases. It is obvious that the smaller the amounts of water per addition, the more accurately the maximum level may be determined. Additions of water, which increase the level of water in the first cell by 0.2% by weight per addition are preferable in many occasions. However, this incremental increase per addition may be decided based on the particular circumstances. If for example there is a relatively large gap between the maximum level of water, over which maximum level the substantially single liquid phase is transformed to two liquid phases, and the minimum level under which minimum level catalyst precipitates, then the additions may be rather large as compared to additions when said gap is relatively small. If the added water necessary for formation of a second liquid phase is less than 10% by weight of the total water contained in the cell, then the maximum level of water is being approached and water is preferably removed. Preferably, the added water necessary for formation of a second liquid phase should be controlled to be more than 20% by weight of the total water contained in the cell. This is true, not only with regard to the above referenced cell, but also to any type of technique used to determine the maximum water level necessary above which formation a second liquid phase occurs. Such techniques include, but are not limited to, computer calculations using phase diagrams, flow sheets, flow sheet simulations, energy balances, etc., well known to the art. Regarding the term "approach", similar principles apply to other ingredients, such as hydrocarbon and/or catalyst, for example, regarding percentages of additional ingredient required for a second liquid phase to be formed or catalyst to precipitate. Thus, the level of hydrocarbon and/or catalyst (at which a second liquid phase is formed or catalyst precipitates) is being approached if an additional 10% of hydrocarbon and/or catalyst is required, at or over which, a second liquid phase is formed or catalyst precipitates.

In order to determine the minimum level of water level in the reaction zone 114, under which minimum level catalyst precipitates, a number of techniques may be used, such as for example taking a sample from the reaction zone, and removing water by azeotropic distillation along with solvent and hydrocarbon, recycling the solvent and hydrocarbon back to the sample at the operational temperature of the reaction zone, continuing this process to the point of catalyst precipitation, and analyzing the composition of the sample. Although this process is capable of determining the minimum level of water, under which minimum level of water catalyst precipitates, it is somewhat cumbersome and complicated.

According to this invention, a substantially better and faster process is one which utilizes the monitor 156, better shown in FIGS. 10 and 11.

A sample of flowable matter taken from the reaction zone 114 is introduced into the second cell 164 of monitor 156 through line 156', in an amount to occupy most of the volume of the second cell 164 for the same reasons given earlier regarding the first cell 162.

At the operation temperature in the reaction zone 114, an adequate amount of water is present so that no precipitation of catalyst occurs, and therefore, the sample received in the second cell 164 is clear (FIG. 10). This fact is detected by the second detector 168. If for any reason at all, catalyst has precipitated in the reaction zone 114, it is desirable to filter out the catalyst precipitate and/or increase the feed rate of the water (provided that second liquid phase formation does not occur with such increase in the feed of the water), preferably from the lower phase 136 of the decanter 132 to avoid further precipitation.

As aforementioned, it has been found that there is an unexpected precipitation of catalyst at elevated temperatures at low water levels and relatively high levels of hydrocarbon and catalyst in a single liquid phase region. It has also been found that there is a correlation between the temperature at and over which the catalyst undergoes precipitation, and the water level at and under which the catalyst undergoes precipitation. Thus, observation of temperature at which the catalyst precipitates may be used as a guide to judge whether or not the water level has to be adjusted in order to avoid catalyst precipitation.

The temperature in the second cell 164 is initially maintained the same as in the reaction zone 114. Then, it is gradually raised, preferably at a rate of about 1° C. per minute. If precipitation of catalyst occurs within a predetermined rise in temperature (the predetermined rise depending on the nature of the reaction zone, approximate composition at which the reaction is being conducted, the degree of control on the water level, and other parameters which can easily be determined in each particular case), the minimum water level under which catalyst precipitates has been approached closely, and the water feed has to be increased to avoid catalyst precipitation in case even minor spontaneous decrease in the water level or increase in temperature occurs in the reaction zone. The amount of increase is determined by also considering the maximum level of water in the reaction zone, determined by the upper water level monitor 154. Preferably the feed of water should be increased in a manner that the water level in the reaction zone 114 reaches and is maintained close to a middle level between the maximum and minimum water levels. However, under certain circumstances, it may be desirable that the water level is closer to the maximum level, or under other circumstances it may be preferable that the water level is maintained closer to the minimum level. In the case that the rise in temperature is higher than 20° C. for catalyst precipitation, no correction in water level is usually required. For in-between temperature rises, careful watch is required, and the water level may be raised somewhat, if this raising of the water level does not come close to the maximum water level over which a second liquid phase is formed. The catalyst precipitation renders the contents of the second cell 164 at least turbid, if not substantially non-transparent, which is detected by the second detector 168 (FIG. 11). In case of turbidity or light absorbency measurements, the catalyst precipitation may be differentiated from second liquid phase formation (and probable emulsification of one liquid phase within the other liquid phase) by the fact that the catalyst may precipitate upon raising the temperature, while a second liquid phase may be formed upon lowering the temperature. Thus, in the former case, clear contents of the cell may become turbid or light-absorbent upon raising the temperature, while in the latter case, clear contents of the cell may become turbid or absorbent upon lowering the temperature.

Figure 12:
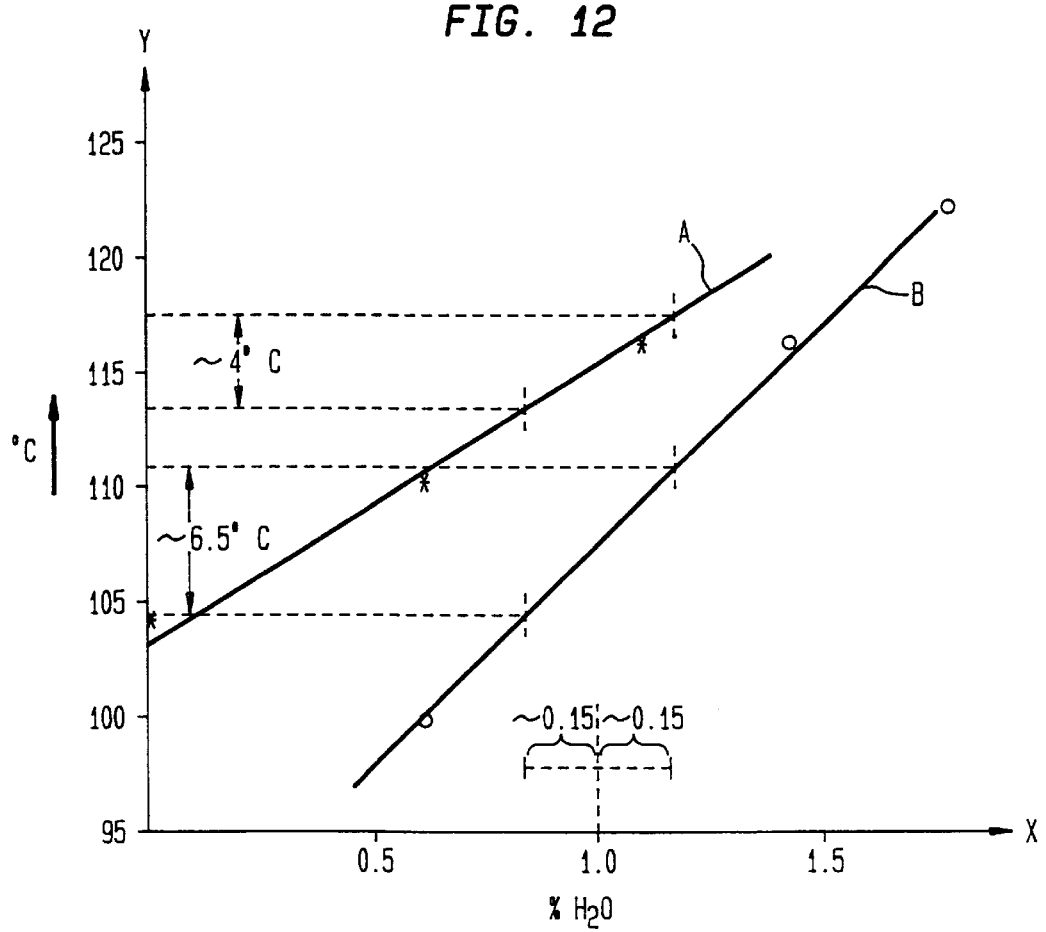
FIG. 12 shows a chart, which illustrates an example on how the predetermined rise in temperature in the second cell of the monitor of FIG. 10 may be determined.

A method by which the aforementioned predetermined rise in temperature may be determined is exemplified and illustrated in FIG. 12, which represents a chart, the X axis of which is water level at or under which catalyst precipitated, and the Y axis is temperature at which the catalyst precipitated, in experiments described below and performed in a cell similar to the second cell 164. In this particular case, the amount of catalyst (cobalt(II) acetate tetrahydrate) present was 4%, the water as indicated on the X axis, and the solvent (glacial acetic acid) plus hydrocarbon (cyclohexane) constituted the rest of the composition. The crystalline water of cobalt(II) acetate tetrahydrate was not included in the amount of water indicated by the X axis. The crystalline water is accounted for as part of the cobalt(II) acetate tetrahydrate. All percentages are by weight and are based on the total of hydrocarbon plus solvent plus catalyst plus water. Line A corresponds to a ratio (by weight) of acetic acid to cyclohexane of 60:40, while line B corresponds to a ratio (by weight) of acetic acid to cyclohexane of 50:50. Although in this example only 4 components were present and were considered, products, by-products of oxidation, as well as other additional components may be present, without changing the method, for all practical purposes.

If now, for the purposes of an example, we assume that the concentration of water in the reaction zone 114 is 1% (excluding the crystalline water of the cobalt(II) acetate tetrahydrate) in a given situation, and the possible control of water level, or maximum deviation, is ±0.15%, the variation in water level may be at most from 0.85% to 1.15%. This variation of water level, corresponds to about 4° C. variation in the case of line A (acetic acid to cyclohexane weight ratio of 60:40) or to about 6.5° C. variation in the case of line B (acetic acid to cyclohexane weight ratio of 50:50). Therefore, if the operator (or the controller) obtains information from cell 164 of monitor 156 (FIGS. 10 and 11) that it takes more than about 4° C. over the first temperature (temperature in the reaction zone 114 and of the contents of cell 164) to cause precipitation of catalyst in cell 164, in the case that the solvent to hydrocarbon ratio is about 60:40, then no addition of water in the reaction zone is necessary to ensure that the catalyst will remain in solution. Similarly, in the case of line B, where the solvent to hydrocarbon ratio is about 50:50, if the operator (or the controller) obtains information from cell 164 of monitor 156 that it takes more than about 6.5° C. over the first temperature to cause precipitation of catalyst in cell 164, then no addition of water in the reaction zone is necessary to ensure that the catalyst will remain in solution. If the temperature rises are smaller than the temperature variations mentioned above for catalyst to be precipitated, then the minimum level of water, under which catalyst is precipitated, is being approached and the water content in the reaction zone has to be increased.

Thus, the controller 122 receives respective information from the first monitor 154 and the second monitor 156, and after processing it according to a predetermined program, it causes appropriate adjustments to the water feed (recycle or fresh feed) so that the water level in the reaction zone 114 is controlled to be within a range between the desired maximum and minimum limits, as already discussed. Programming of controllers is very well known to the art.

It is possible that in some occasions, especially in the case of excessive amounts of hydrocarbon, such as cyclohexane for example, and catalyst, such as cobalt(II) acetate tetrahydrate for example, the "maximum" level of water over which a second liquid phase is formed at operation temperature, is actually lower that the "minimum" water level under which catalyst precipitates at operating temperature. In such occasions, the operation of the reaction zone may only be conducted at a water level lower than the maximum level of water over which a second liquid phase is formed in the presence of precipitated catalyst. Otherwise, if it is desirable, either the hydrocarbon level is decreased or the catalyst level is decreased, or both, so that the level of water at which the precipitation of catalyst occurs decreases and the level at which a second liquid phase is formed increases.

In any case, when under a given set of conditions, the level of water at which or below which the catalyst precipitates is higher than the level of water at which or over which a second liquid phase is formed, there is no single liquid phase range within which a single liquid phase without precipitated catalyst exists.

The instant invention applies particularly well to cases where the hydrocarbon is cyclohexane, the solvent is acetic acid and the catalyst is cobalt(II) acetate tetrahydrate. The water level at which catalyst precipitation occurs decreases as the cyclohexane content and/or the catalyst content decrease. The water level at which a second liquid phase formation occurs increases as the cyclohexane content and/or the catalyst content decrease. Thus, with decrease in cyclohexane content and the catalyst content, the gap between the maximum level of water, over which maximum level the substantially single liquid phase is transformed to two liquid phases, and the minimum level under which minimum level catalyst precipitates, is broadened and the control of the water level adjustments is facilitated. However, at the same time the reaction rate and reactivity (reaction rate is defined as the molar oxidation of hydrocarbon per unit of time, and the reactivity defined as the reaction rate per total volume of mixture involved in the reaction) decrease. Thus, a compromise has to be made depending on the particular circumstances.

The most vulnerable region, which may greatly benefit from the teachings of the instant invention corresponds to cases wherein the cyclohexane to acetic acid ratio is in the range of about 30/70 to about 60/40. This is a very important range for the direct oxidation of cyclohexane to adipic acid in an operation temperature range of 80° to 120° C.

At a cobalt(II) acetate tetrahydrate level of about 4%, the following have been visually observed in a cell similar to the first cell 162 and second cell 164, shown in FIGS. 8 and 8A, respectively, but lacking the first detector 166 and the second detector 168, respectively. It should be noted that in all three cases (A), (B), and (C), the level of catalyst was 4% by weight, based on the sum of catalyst plus solvent (acetic acid) plus hydrocarbon (cyclohexane) plus water (excluding the crystalline water of the cobalt(II) acetate tetrahydrate, which crystalline water was taken as part of the catalyst. All levels in these cases were also calculated the same way.

(A) at 90° C.:

(1) at a cyclohexane to acetic acid ratio of 60 to 40, a second liquid phase was formed at about and over 0.1% water level, and catalyst precipitated at about and under the same water level; therefore, there is no practical range within which a single liquid phase without precipitated catalyst exists;

(2) at a cyclohexane to acetic acid ratio of 50 to 50, catalyst precipitation occurred at a water level of about and under 0.25%, while a second liquid phase was formed at a water level of about and over 1%; therefore the water level in a reaction zone would have to be controlled at a higher level than about 0.25% to prevent catalyst precipitation and a lower level than about 1% to prevent formation of a second liquid phase;

(3) at a cyclohexane to acetic acid ratio of 40 to 60, no catalyst precipitation occurred even at a water level of 0%, while a second liquid phase was formed at a water level of about and over 2%; therefore the water in a reaction zone would have to be controlled at a level lower than about 2% to prevent formation of a second liquid phase without any problem of catalyst precipitation;

(4) at a cyclohexane to acetic acid ratio of 30 to 70, no catalyst precipitation occurred even at a water level of 0%, while a second liquid phase was formed at a water level of about and over 3%; therefore the water in a reaction zone would have to be controlled at a level lower than about 3% to prevent formation of a second liquid phase without any problem of catalyst precipitation;

(B) at 100° C.:

(1) at a cyclohexane to acetic acid ratio of 60 to 40, a second liquid phase was formed at about and over 0.15% water level, while catalyst precipitated at about and under 0.6% water from a two liquid phase system; therefore, there is no range thin which a single liquid phase without precipitated catalyst exists);

(2) at a cyclohexane to acetic acid ratio of 50 to 50, catalyst precipitation occurred at a water level of about and under 0.9%, while a second liquid phase was formed at a water level of about and over 1.4%; therefore the water level in a reaction zone would have to be controlled at a higher level than about 0.9% to prevent catalyst precipitation and a lower level than about 1.4% to prevent formation of a second liquid phase;

(3) at a cyclohexane to acetic acid ratio of 40 to 60, catalyst precipitation occurred at a water level of about and under 0.1%, while a second liquid phase was formed at a water level of about and over 2.3%; therefore the water level in a reaction zone would have to be controlled at a higher level than about 0.1% to prevent catalyst precipitation and a lower level than about 2.3% to prevent formation of a second liquid phase;

(4) at a cyclohexane to acetic acid ratio of 30 to 70, no catalyst precipitation occurred even at a water level of 0%, while a second liquid phase was formed at a water level of about and over 4.1%; therefore the water in a reaction zone would have to be controlled at a level lower than about 4.1% to prevent formation of a second liquid phase without any problem of catalyst precipitation;

(C) at 110° C.:

(1) at a cyclohexane to acetic acid ratio of 60 to 40, a second liquid phase was formed at about and over 0.2% water level, while catalyst precipitated at about and under 0.8% water from a two liquid phase system; therefore, there is no range within which a single liquid phase without precipitated catalyst exists);

(2) at a cyclohexane to acetic acid ratio of 50 to 50, catalyst precipitation occurred at a water level of about and under 1.4%, while a second liquid phase was formed at a water level of about and over 1.9%; therefore the water level in a reaction zone would have to be controlled at a higher level than about 1.4% to prevent catalyst precipitation and a lower level than about 1.9% to prevent formation of a second liquid phase;

(3) at a cyclohexane to acetic acid ratio of 40 to 60, catalyst precipitation occurred at a water level of about and under 0.8%, while a second liquid phase was formed at a water level of about and over 3.2%; therefore the water level in a reaction zone would have to be controlled at a higher level than about 0.8% to prevent catalyst precipitation and a lower level than about 3.2% to prevent formation of a second liquid phase;

(4) at a cyclohexane to acetic acid ratio of 30 to 70, catalyst precipitation occurred at a water level of about and under 0.2%, while a second liquid phase was formed at a water level of about and over 5.6%; therefore the water level in a reaction zone would have to be controlled at a higher level than about 0.2% to prevent catalyst precipitation and a lower level than about 5.6% to prevent formation of a second liquid phase;

(5) at a cyclohexane to acetic acid ratio of 20 to 80, no catalyst precipitation occurred even at a water level of 0%, while a second liquid phase was formed at a water level of about and over 8%; therefore the water in a reaction zone would have to be controlled at a level lower than about 8% to prevent formation of a second liquid phase without any problem of catalyst precipitation;

It should be understood, however, that in either case of the determination of the maximum or minimum levels of water described above, samples may be taken manually and/or examined visually to detect two liquid phase formation and/or catalyst precipitation, and the results of such determination be fed to the controller 122, or the feeds changed manually.

Going back to FIG. 8, the monitor 154 may be used for other purposes in addition to determining the maximum level of water over which a second liquid phase is formed.

As aforementioned, the monitor 154 may be used for determining the maximum level of water over which a second liquid phase is formed. However, it may also be used to predict formation of a second liquid phase under many other circumstances involving ingredients other than water.

Thus, in a different embodiment of the present invention, a sample of flowable material from the reaction zone 114 is transferred to the first cell 162, and it is maintained at the same temperature as the operation temperature of the reaction zone 114. In sequence, small amounts of hydrocarbon, cyclohexane for example, are added incrementally to the first cell 162, and mixed well with its contents. After each increment of hydrocarbon is added and mixed, the first cell 162 is allowed to stand still for a short period of time, preferably ½ to 1 minute, and the first detector scans the cell as previously described to detect whether a second liquid phase has been formed. Depending on the amount of added hydrocarbon for a second liquid phase to be formed, the operator, or the program of the controller may decide whether to make any adjustments to the feed of hydrocarbon, or even other feeds, or other conditions, in order to ensure the maintenance of a substantially single liquid phase in the reaction zone 114. Preferably, if less than 3% by weight increase in hydrocarbon concentration (based on total contents of the first cell 162) causes formation of a second liquid phase, immediate action is preferably taken to prevent possible eminent formation of a second liquid phase in the reaction zone. If, for example, the total contents of the first cell 162 are X grams, the preferable maximum addition of hydrocarbon causing formation of a second liquid phase (before action should be taken) would be 3X/(100−3)=3X/97. The type of action may be, for example, decrease of hydrocarbon, such as cyclohexane for example, in the reaction zone, decrease of water level in the reaction zone, decrease of catalyst, such as cobalt(II) acetate tetrahydrate for example, in the reaction zone, increase of solvent, such as acetic acid for example, in the reaction zone, increase of operation temperature in the reaction zone, etc.

In still a different embodiment of the present invention, a sample of flowable material from the reaction zone 114 is transferred to the first cell 162, and it is maintained at the same temperature as the operation temperature of the reaction zone 114. In sequence, small amounts of catalyst, cobalt(II) acetate tetrahydrate for example, are added incrementally to the first cell 162, and mixed well with its contents. After each increment of catalyst is added and mixed, the first cell 162 is allowed to stand still for a short period of time, preferably ½ to 1 minute, and the first detector scans the cell as previously described to detect whether a second liquid phase has been formed. Depending on the amount of added catalyst for a second liquid phase to be formed, the operator, or the program of the controller may decide whether to make any adjustments to the feed of hydrocarbon, or even other feeds, or other conditions, in order to ensure the maintenance of a substantially single liquid phase. Preferably, if less than 0.5% by weight increase in catalyst (based on total contents of the first cell 162)

causes formation of a second liquid phase, immediate action is preferably taken to prevent possible eminent formation of a second liquid phase. The type of action may be, for example, decrease of hydrocarbon, such as cyclohexane for example, in the reaction zone, decrease of water level in the reaction zone, decrease of catalyst, such as cobalt(II) acetate tetrahydrate for example, in the reaction zone, increase of solvent, such as acetic acid for example, in the reaction zone, increase of operation temperature in the reaction zone, etc.

Further, in another embodiment of the present invention, a sample of flowable material from the reaction zone 114 is transferred to the first cell 162, and it is initially maintained at the same temperature as the operation temperature of the reaction zone 114. In sequence, the temperature of the contents of the first cell 162 is dropped gradually, preferably at a rate of about 1° C. per minute. If formation of a second liquid phase occurs within a predetermined decrease in temperature, preferably 5° C., immediate action is preferably taken to prevent possible eminent formation of a second liquid phase. The type of action may be, for example, decrease of hydrocarbon, such as cyclohexane for example, in the reaction zone, decrease of water level in the reaction zone, decrease of catalyst, such as cobalt(II) acetate tetrahydrate for example, in the reaction zone, increase of solvent, such as acetic acid for example, in the reaction zone, increase of operation temperature in the reaction zone, etc. In the case that the decrease in temperature is higher than 20° C. for second liquid phase formation, no correction is usually required. For in-between temperature decreases for second liquid phase formation, careful watch is required.

In another embodiment, the effect of addition of more than one of water, hydrocarbon, catalyst, and solvent, in desired quantities through line 154", may also be determined and the information used, if so desired, to be fed to the controller 122 for processing and further action. More than one cells of the type of cell 162 may be used so that the effect of additional water, hydrocarbon, catalyst, etc., on formation of a second liquid phase may be determined faster. The effect of solvent in one or more cells may be determined, if the solvent is added before or after the second liquid phase formation in the cell. Similar results may be achieved by changing the temperature up and/or down.

Of course, any combination of one or more of hydrocarbon, solvent, catalyst, water, initiator, other matter, etc. (without coming from a reaction zone) may be used in the first cell 162 of FIG. 8, at a desired temperature, for detection of a second liquid phase presence. Further, formation of a second liquid phase, at a desired temperature, by addition of any combination of one or more of hydrocarbon, solvent, catalyst, water, initiator, other matter, into the first cell 162, containing a pre-existing single liquid phase mixture of components (for example hydrocarbon, solvent catalyst, water, initiator, other matter, etc.), may be observed and/or studied. In addition, any such combination may be examined for the temperature at which a second liquid phase may be formed, by varying the temperature of the first cell. Similarly, by raising the temperature in cell 163 from a lower temperature at which the catalyst is soluble, to a desired higher temperature, a catalyst precipitation temperature may be determined, if such a temperature exists within the range of the lower temperature to the desired higher temperature.

As aforementioned, the instant invention also pertains a method of maintaining in a reaction zone, reaction zone 114 for example, a substantially single-phase liquid mixture comprising a hydrocarbon at a first hydrocarbon level, a catalyst at a first catalyst level, a solvent at a first solvent level, and water at a first water level, the method comprising the steps of:

(a) contacting the liquid mixture, at least part of which enters the reaction zone, reaction zone 114 for example, through line 116 for example, with a gaseous oxidant entering the reaction zone 114 through line 118 for example, the temperature in the reaction zone being a first temperature, adequately high for the oxidation to proceed;

(b) taking a sample from the reaction zone 114 into a cell 162 for example;

(c) lowering the temperature of the sample to a predetermined second temperature, and if a second liquid phase is formed (as detected by the scanning detector 166 for example) at a critical temperature in the range between the first and second temperatures, either decrease in the reaction zone, reaction zone 114 for example, the first level of one component selected from a group consisting of hydrocarbon, water, catalyst, and a mixture thereof to a degree that in a new sample, a second liquid phase does not form in the range between the first and second temperatures, or increase in the reaction zone the first solvent level to a degree that in a new sample a second liquid phase does not form in the range between the first and second temperatures, or increase in the reaction zone the first temperature to a third temperature by at least the difference between the critical temperature and the second temperature, or a combination thereof.

In one example, if the first temperature in the reaction zone is 100° C., the second predetermined temperature is 95° C., and the second liquid phase formation occurred at a critical temperature of 98° C., the first temperature should be raised to be higher than 103° C. (100+98−95).

Raising the first temperature to the third temperature is undesirable in the case that catalyst precipitates in the range between the first and the third temperatures.

It should be understood that according to the present invention, any liquids or gases or off-gases may be recycled totally or partially from any section to any other section.

According to the present state of the art, after a reaction has taken place in the Direct Synthesis of cyclohexane to adipic acid, a mixture of two liquid phases are present at ambient or lower temperatures, along with a solid phase mainly consisting of adipic acid. The two liquid phases have been called the "Polar Phase" and the "Non-Polar Phase". The two phases are decanted, and the adipic acid is further crystallized and separated from the "Polar Phase".

The presence of two liquid phases mixed with a solid phase and the precipitating acid from the "Polar Phase" along with the required filtration of the solid phase cause a very undesirable situation. Decanting itself is an undesirable additional step in a process, even if it is performed in the absence of a solid phase. The simultaneous presence of a solid phase, especially if part of the solid is dissolved in one of the liquid phases, and apt to precipitate upon any lowering of the temperature, or with time, brings about serious complications.

The inventors of the instant invention, have discovered that they can avoid the formation of a two-phase liquid system, and maintain a single liquid phase containing the solid phase, even at ambient or lower temperature using the techniques and devices described in detail hereinbelow. The absence of a second liquid phase, not only eliminates a decanting step, but also simplifies the whole process of separating the solid phase from the single liquid phase.

In addition to the formation of adipic acid, the methods of the present invention may also be applied to other dibasic acids from the corresponding cyclic aliphatic hydrocarbons. Examples are formation of glutaric acid from cyclopentane, formation of pimelic acid from cycloheptane, and the like.

Figure 13:
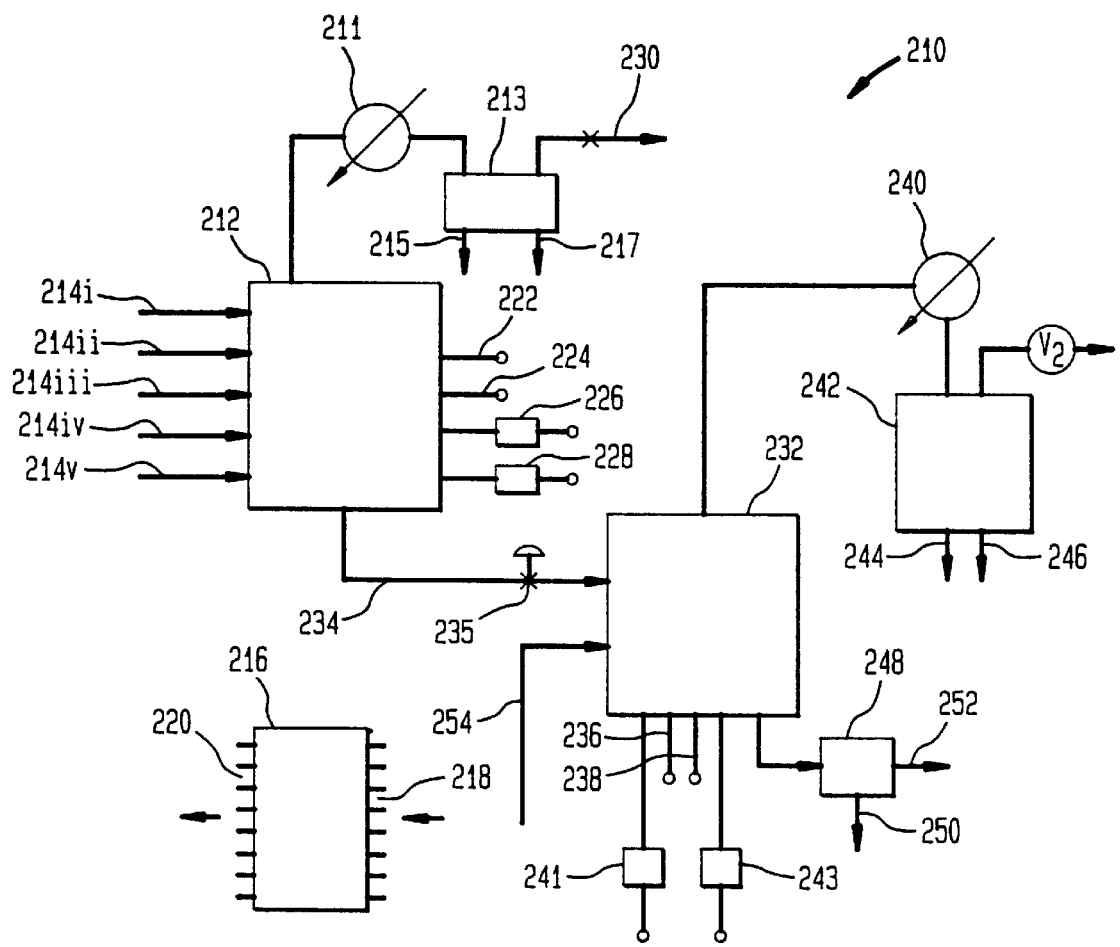
FIG. 13 illustrates a block diagram of another preferred embodiment of the present invention, comprising a first reaction chamber and a second chamber.

Referring now to FIG. 13, there is depicted a device or reactor system according to a preferred embodiment of the instant invention. The device or reactor system 210 comprises a first reaction chamber 212.

The first reaction chamber 212 is connected to a first condenser 211, which in turn is preferably connected to a first retaining chamber 213. The first retaining chamber 213 may also play the role of a decanter, for separating, for example, water of reaction and/or solvent from mainly hydrocarbon through lines 215 and 217, respectively, for example.

Any type of condenser may be used with the miscellaneous chambers of the instant invention, including but not limited to spray condensers, shell and tube heat exchangers, etc.

A number of controlled feeding lines or feeding means are connected to the first reaction chamber 212. These controlled feeding lines or means are a first hydrocarbon feeding line 214$i$, a first gaseous oxidant feeding line 214$ii$, a first solvent feeding line 214$iii$, a first catalyst feeding line 214$iv$, and a first initiator feeding line 214$v$. Feeding the respective materials through these controlled feeding lines or feeding means, is controlled by a controller 216, having inputs 218 and outputs 220. Flow rate information from each feeding line is provided to the controller 216 by flowmeters (not shown for purposes of clarity) connected to inputs 218 by well known to the art techniques. Valves or pumps or a combination of both (not shown for purposes of clarity) are connected to respective outputs 220, through which the controller 216 controls the feed rates of the different streams after processing the flow rates information as well as additional information, such as temperature, pressure, analytical data, etc., according to a desired program. The aforementioned feeding lines may merge individually or together, in part or totally, to pre-reaction chamber(s) (not shown) or vessels (not shown), or heat exchangers (not shown), all well known to the art, before they enter the first reaction chamber 212. Such arrangements may be also controlled by the controller 216 through output lines 220.

Connected to the first reaction chamber 212, there are also a temperature monitor 222, and a pressure monitor 224, both connected (not shown) in turn to input lines 218 of the controller 216.

The temperature input obtained by the controller 216 is useful for miscellaneous heat exchangers (not shown), such as heaters and/or coolers (including condensers) for example, either directly connected to the first reaction chamber 212, or through line 230, or through any arrangement of the feeding lines 214$i$ to 214$v$, to be controlled by the controller 216 through outputs 220 and thus adjust the temperature in the first reaction chamber. This combination provides an example of a first temperature control means for controlling the temperature inside the first reaction chamber 212.

The pressure input obtained by the controller 216 is useful for miscellaneous valves, and/or pumps, etc. (not shown), to be controlled by the controller 216 through outputs 220 and thus adjust the pressure in the first reaction chamber according to a predetermined manner. This combination provides an example of a first pressure control means for controlling the pressure inside the first reaction chamber 212.

Preferably, a chemical analytical monitor 226 is also connected to the first reaction chamber 212 for receiving samples of the contents of said first reaction chamber 212, analyzing them, and providing the analysis information to the controller 216, again through input lines 218. The chemical analyzer 226 preferably comprises GC and HPLC instrumentation, and more preferably GC/MS, GC/FID, HPLC/UV and HPLC/MS, for obtaining fast and accurate chemical balances to be provided to the controller 216 for being used for further processing, and finally to be used for the control of the miscellaneous parameters and conditions involved in the operation of the first reaction chamber 212.

Also preferably, a phase analyzer or monitor 228, as described earlier, is connected to the first reaction chamber 212 for receiving samples of the contents of said first reaction chamber 212, phase-analyzing them, and providing the analysis information to the controller 216, again through input lines 218. The results are then provided to the controller 216 for being used for further processing, and finally to be used for the control of the liquid phase conditions inside the first reaction chamber 212.

An off-gas outlet 230 is further connected to the first retaining chamber or decanter 213 for removing off-gases by well known to the art techniques.

The first reaction chamber 212 communicates with a second chamber 232 through a first transfer line 234, which first transfer line 234 comprises a valve 235. Preferably, connected to the second vessel 232, there are a second temperature monitor 236, a second pressure monitor 238, a second chemical analyzer 241, and a second phase analyzer 243. In a similar manner as in the case of monitoring the different parameters of the first reaction chamber 212, the second temperature monitor 236, the second pressure monitor 238, the second chemical analyzer 241, and the second phase analyzer 243 are connected to inputs 218 to provide information and enable the controller 216 to control respective parameters and conditions of the contents of the second chamber 232. Thus, they provide means for controlling the second temperature and the second pressure in the second chamber 232, while maintaining a single liquid phase.

Although for continuous reactor systems the first reaction chamber 212 and the second chamber 232 should be individual units, in the case of batch reactors they may be combined in one and the same unit, preferably utilizing only one set of monitors and analyzers.

The second chamber 232 is also connected to a second condenser 240, which in turn is preferably connected to a second retaining chamber 242. The second retaining chamber 242 may also play the role of a decanter, for separating, for example, water of reaction and/or solvent from mainly hydrocarbon through lines 244 and 246, respectively, for example. A vacuum generator V2 may preferably be also connected to the second retaining chamber 242.

The second chamber 232 is preferably further connected to separating means, such as a solids separator 248, for example, for separating at least partially the dibasic acid. Such solids separators may be for example pressure-filtering devices, centrifugal devices, etc. The solids may be transferred out of the solids separator 248 through a solids line 250, and the liquids may be transferred out of the solids separator 248 through a liquids line 252.

A second hydrocarbon feeding line 254 is preferably provided with a flowmeter which gives flow information to input 18 of the controller 216, and it is connected to the second chamber 232. It preferably originates from a hydrocarbon supply vessel (not shown) through pumps and/or valves (not shown), which are connected to output lines 220 and are controlled by the controller 216. The hydrocarbon, such as cyclohexane for example, may be provided to line 254 from line 246, or any other appropriate line or source.

In operation of this embodiment, hydrocarbon, such as cyclohexane for example enters the first reaction chamber 212 through the hydrocarbon feeding line 214$i$. Gaseous oxidant, such as oxygen or a mixture of oxygen with an inert gas for example enters the reaction chamber 212 through the gaseous oxidant feeding line 214$ii$. Solvent, such as acetic acid for example, enters the first reaction chamber 212 through the solvent feeding line 214$iii$. Catalyst, such as a cobalt compound for example, enters the first reaction chamber 212 through the catalyst feeding line 214$iv$. Initiator, such as acetaldehyde or cyclohexanone for example, enters the first reaction chamber 212 through the initiator feeding line 214$v$. As aforementioned, the feeding of the above raw materials does not have to take place directly to the reaction chamber 212. Some or all of the raw materials may be premixed, pre-heated, pre-cooled, or otherwise treated before entering the reaction chamber 212, by techniques well known to the art, or as described in our aforementioned patents and patent application. Mixtures of re-cycled products and/or by-products may also be introduced to the reaction chamber 212, individually or combined with one or more of the fresh raw materials. If the recycling process provides adequate amounts of any of the raw materials, then no additional feed is necessary. The first temperature and the first pressure are arranged by the controller to be such that a reaction of hydrocarbon, cyclohexane for example, and oxidant, oxygen for example, takes place in a controlled manner. Preferable partial first pressures of oxidant are in the range of 10 to 500 psig, and first temperatures in the range of 60° C. to 160° C. These preferable ranges, however, depend on the nature of hydrocarbon and oxidant. In the case that the hydrocarbon is cyclohexane and the oxidant is oxygen, the preferable range of first temperatures is 80° C. to 120° C. An even more preferable range is 90° C. to 110° C.

It is highly preferable that the contents of the reaction chamber 212 comprise just a single liquid phase. The chemical analyzer 226 and/or the phase analyzer 228 give information to the controller 216, which is utilized to ensure the single liquid phase condition, if so desired. Although it is preferable not to have suspended solids at this stage, the existence of a solid phase suspended within the single or even double liquid phase is not excluded.

Preferably, part of the contents of the first reaction chamber 212 is being transferred to the second chamber 232 through first transfer line 234, where it is being cooled to a second temperature, lower than the first temperature of the first reaction chamber 212. At the second temperature, preferably precipitation of product of oxidation, such as adipic acid for example, occurs. The second temperature is preferably ambient (about 20° C.) or lower, but not lower than the freezing point of the liquid contents of the second chamber 232. The second temperature is monitored by the second temperature monitor 236, and the temperature information is provided to the controller 216 for further processing.

In some occasions, such as in the case of atomization reaction chambers for example, it is also preferable that another part of the contents of the reaction chamber 212 are recirculated (not shown) from line 234 back to the first reaction chamber 212, preferably through atomization nozzles.

According to the present invention, it is also necessary that despite the fact that the second temperature is lower, and preferably considerably lower, than the first temperature, no second liquid phase is allowed to be formed. By not allowing a second phase to be formed, an undesirable decanting step, especially in the presence of a solid precipitated phase, and its consequences are completely eliminated.

The second temperature may be controlled in a number of different ways. A highly preferable way is by controllably reducing the pressure in the second chamber 232 to attain a value preferably considerably lower than the value of the first pressure prevailing in the first reaction chamber 212. By doing this, two very desirable phenomena take place. First, the temperature is being lowered by evaporation of volatiles, such as cyclohexane or other hydrocarbon for example, due to the reduction of pressure. Second, evaporation of hydrocarbon results in lowering the content of hydrocarbon in the mixture, which favors a single liquid phase. The lowering of hydrocarbon content has to be high enough for maintaining the single liquid phase at the second temperature. If the initial content of the first reaction chamber 212 is low enough, and/or if the conversion of hydrocarbon to dibasic acid is high enough, then there is no need for large amounts of hydrocarbon to be removed from the contents of the second chamber 232 in order to maintain a single liquid phase. In such a case, even additional cold hydrocarbon or other cold matter may be added to the second chamber 232 through the second hydrocarbon feeding line 254 without formation of a second liquid phase. Such matter may preferably be solvent or hydrocarbon.

The hydrocarbon evaporated from the second chamber 232 along with solvent, water, and other gases and/or vaporized liquids is condensed in the second condenser 240, and collected in the second retaining chamber 242, where the water with solvent may be separated from the hydrocarbon with solvent and, either one or both, recirculated (for example to the first reaction chamber 212 or to the second chamber 232) or otherwise treated through lines 244 and 246.

Additional cooling may be provided, if necessary, to the contents of the second chamber 232, by well known to the art techniques, so that at least part, and preferably the majority of the dibasic acid, adipic acid for example, precipitates. In turn, the dibasic acid is separated in solids separator 248, by filtration for example, or any other method well known to the art. The solids are transferred out of the solids separator 248 through solids line 250, and the liquids are transferred out of the of the solids separator 248 through liquids line 252 for further treatment and/or recycling.

The temperature of the second chamber 232 may also be managed by adjusting the composition of the contents of said second chamber 232. For example, heat may be added with simultaneous adjustment of hydrocarbon, such as cyclohexane for example, content. Removal of water with cyclohexane favors the formation and maintenance of a single liquid phase. For example, recycling of cyclohexane from the second retaining chamber 242 to the second chamber 232 through line 246, and simultaneous addition of heat to said second chamber 232, by means of a heating coil (not shown) for example, may lower the content of water and/or cyclohexane in the second chamber 232, and thereby promote the formation and maintenance of a single liquid phase. Further, addition of solvent, also favors the formation and maintenance of a single phase.

The second pressure inside the second chamber 232 is preferably maintained as atmospheric or sub-atmospheric through vacuum generator V2. In some occasions further cooling may be achieved in the second chamber 232 by addition of hydrocarbon or other matter having lower temperature than the temperature of the contents of the second chamber 232, through line 254, as also mentioned earlier.

As aforementioned, in a similar manner as in the case of monitoring the different parameters of the first reaction chamber 212, the second temperature monitor 236, the second pressure monitor 238, the second chemical analyzer 241, the second phase analyzer 243, and flowmeters in lines 234 and 254 are connected to inputs 218 to provide information and enable the controller 216 to control respective parameters and conditions of the contents of the second chamber 232. Thus, they provide means for controlling the temperature and the pressure in the second chamber 232, while maintaining a single liquid phase.

Figure 14:
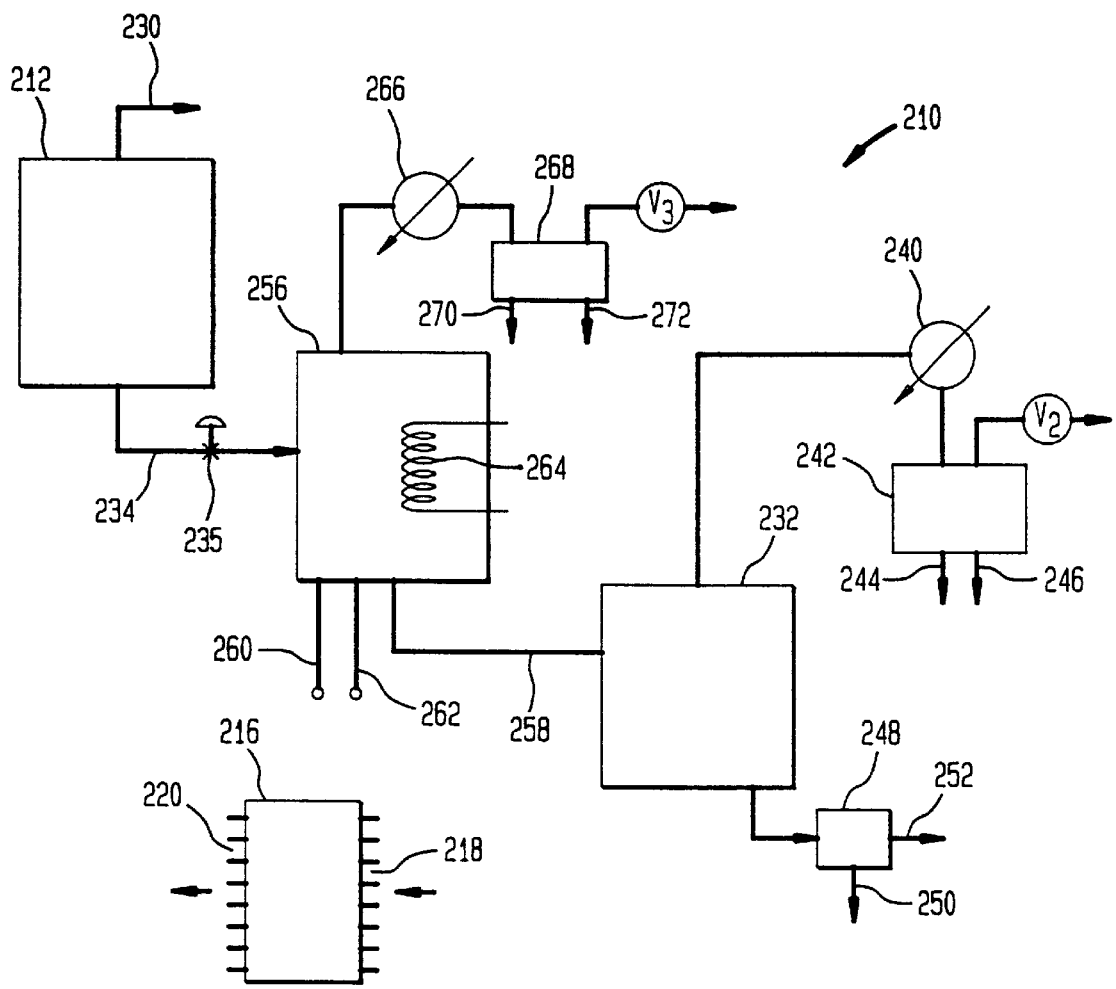
FIG. 14 illustrates a block diagram of still another preferred embodiment of the present invention, wherein external heating means have been provided between the first reaction chamber and the second chamber.

In a different preferred embodiment of the present invention, better illustrated in FIG. 14, the device or reactor system 210, comprises, in addition to the other chambers and their accessory elements, a first intermediate chamber 256, which communicates with the first reaction chamber 212 through the first transfer line 234, and with the second chamber 232 through a second transfer line 258.

To the first intermediate chamber 256, there is also connected a first intermediate temperature monitor 260, which monitor is also connected to inputs 218 of the controller 216 for providing temperature information to said controller, which controller in turn controls the temperature inside the chamber 256. This arrangement constitutes first intermediate temperature control means for controlling the temperature in said first intermediate chamber 256.

To the first intermediate chamber 256, there is also connected first intermediate pressure monitor 262, which monitor is also connected to inputs 218 of the controller 216 for providing pressure information to said controller, which controller in turn controls the pressure inside the chamber 256. This arrangement constitutes first intermediate pressure control means for controlling the temperature in said first intermediate chamber 256.

The intermediate chamber 256, further comprises first intermediate external heating means 264, such as a heating coil for example, for providing thermal energy to matter inside the first intermediate chamber 256. The intermediate chamber 256 is also connected to an intermediate condenser 266, which in turn is preferably connected to an intermediate retaining chamber 268. As in the case of the retainer 242, the retainer 268 may also serve as a simple decanter for separating reaction water and/or solvent through line 270, and mainly hydrocarbon through line 272. An intermediate vacuum generator V3 may also be connected to the intermediate retaining chamber 268.

Decanting liquids in absence of a solid phases is substantially less complicated than decanting in the presence of said solid phases.

The operation of this embodiment is similar to the operation of the previous embodiment with the exception that the first pressure prevailing in the first reaction chamber 212 is controllably dropped to a desired first intermediate pressure in the intermediate chamber 256, forcing hydrocarbon and smaller amounts of other volatile materials, such as for example reaction water and/or solvent, to evaporate and be condensed by intermediate condenser 266, thus lowering the content of hydrocarbon in the first intermediate chamber 256, and also removing heat from the system, resulting in lowering the first temperature to a first intermediate temperature. In a continuous operation, which is the preferred type of operation, a stream of liquid from the first reaction chamber 212 is being transferred to the first intermediate chamber 256 through the first transfer line 234.

The first intermediate external heating means 264, provides a controlled and desired amount of heat to the contents of the first intermediate chamber 56, so that further hydrocarbon evaporates. The temperature and the hydrocarbon content of the first intermediate chamber 256 may be maintained at such levels so that preferably no substantial precipitation of a solid phase comprising dibasic acid occurs. Higher temperatures and lower contents of hydrocarbon favor the prevention of precipitation, as well as the prevailing of a single liquid phase.

A stream of liquid is also being transferred to the second chamber 232 through the second transfer line 258. The rest of the operation is substantially the same as described in the previous embodiment, with the controller programmed to ensure that at the second temperature prevailing in the second chamber 232 and the amount of hydrocarbon are such that there is only a single liquid phase containing the precipitated dibasic acid, adipic acid for example.

Figure 15:
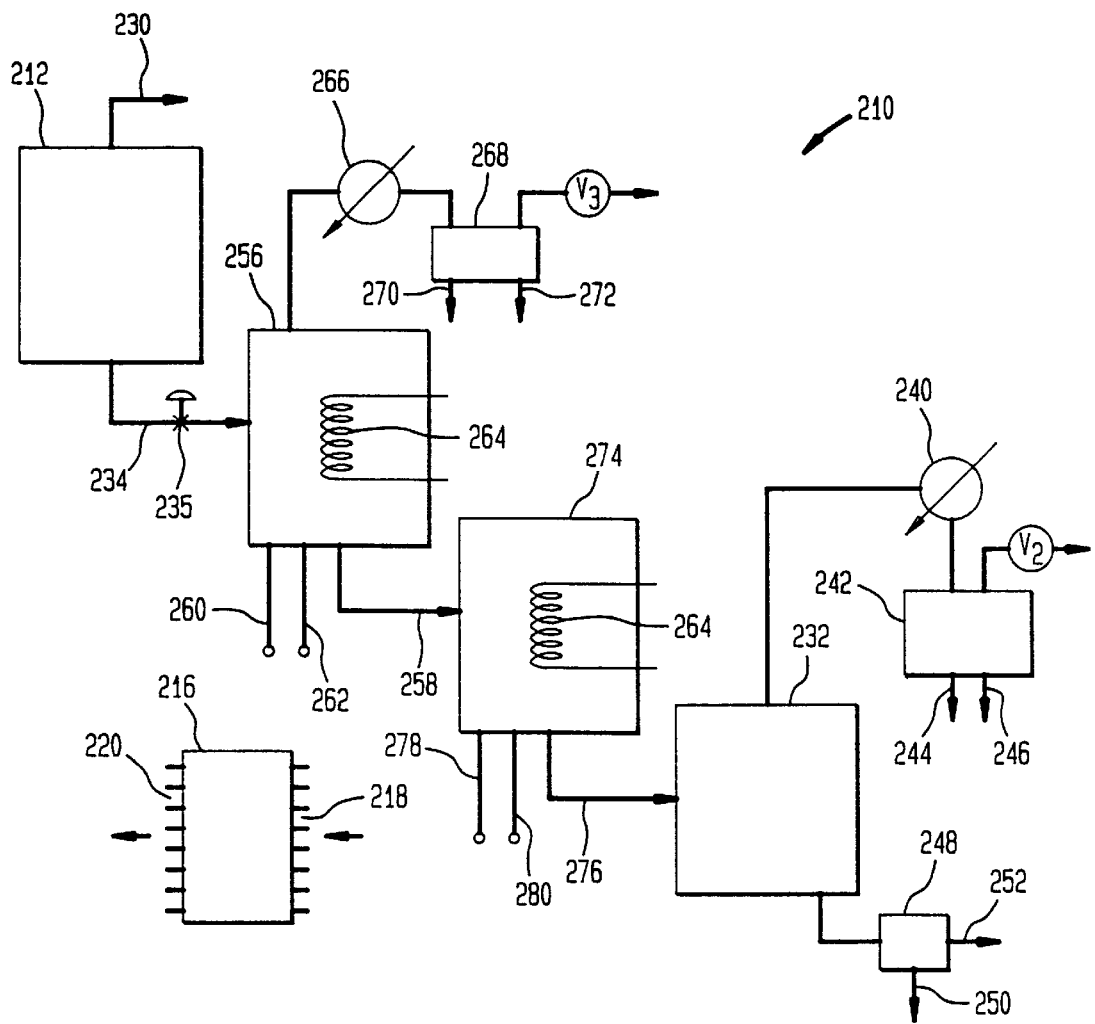
FIG. 15 illustrates a block diagram of still another preferred embodiment of the present invention, wherein both external heating means and external cooling means have been provided between the first reaction chamber and the second chamber.

In a still a different preferred embodiment of the present invention, better illustrated in FIG. 15, the device or reactor system 210, comprises, in addition to the other chambers and their accessory elements, a second intermediate chamber 274, which communicates with the first intermediate chamber 256 through the second transfer line 258, and with the second chamber 232 through a third transfer line 276. Although, for purposes of simplicity, condensers, retaining chambers, vacuum generators, etc., are not shown in all chambers, it should be understood that such elements may be connected to any one of the chambers. In addition, one or more of the vacuum generators may be replaced by let-down valves, open lines, etc.

To the second intermediate chamber 274, there is also connected a second intermediate temperature monitor 278, which monitor is also connected to inputs 218 of the controller 216 for providing temperature information to said controller, which controller in turn controls the temperature inside the chamber 274. This arrangement constitutes second intermediate temperature control means for controlling the temperature in said second intermediate chamber 274.

To the second intermediate chamber 274, there is also connected second intermediate pressure monitor 280, which monitor is also connected to inputs 218 of the controller 216 for providing pressure information to said controller, which controller in turn controls the pressure inside the chamber 274. This arrangement constitutes second intermediate pressure control means for controlling the temperature in said second intermediate chamber 274.

The second intermediate chamber 274, further comprises second intermediate external cooling means 282, such as a cooling coil for example, for removing thermal energy from matter inside the second intermediate chamber 274.

The operation of this embodiment is similar to the operation of the previous embodiments with the exception that the first intermediate temperature prevailing in the first intermediate chamber 56 is reduced in the second intermediate chamber to a second intermediate temperature with substantially no solids precipitation. After addition of heat and removal of an adequate amount of hydrocarbon in the first intermediate chamber 256, heat is removed in the second intermediate chamber 274, so that when the second intermediate pressure, which is preferably the same as the first intermediate pressure, is reduced in the second chamber 232 to the second pressure, the temperature drops adequately for a substantial precipitation of the dibasic acid, adipic acid for example, to occur. Of course, an adequate amount of hydrocarbon, cyclohexane for example, is removed in the first intermediate chamber 256 and the second chamber 232, so that no second liquid phase is formed in the second chamber 232. It is highly preferable to avoid having cooling elements, such as cooling coils for example, in the chamber (in this case second chamber 232) in which the precipitation of the solid phase takes place, since deposits on the coils and plugging problems become a serious problem.

Chemical and/or phase analysis may be conducted on the contents of any of the transfer lines or any of the chambers in any of the embodiments.

It should be understood that according to the present invention, any liquids or gases or off-gases may be recycled totally or partially from any chamber to any other chamber.

A preferable type of controller is a computerized controller, and more preferably a "learning computer" or a "neuro-computer", the functionality of which is known to the art, and which collects information from different places of the device (for example pressure, temperature, chemical or other analysis, etc.), stores this information along with the result (reaction rate, for example), and it is programmed to use this information in the future, along with other data if applicable, to make decisions regarding the action to be taken at each instance.

Although the miscellaneous functions are preferably controlled by a computerized controller, it is possible, according to this invention, to utilize any other type of controller or even manual controls for controlling one or more functions.

Oxidations according to this invention, are non-destructive oxidations, wherein the oxidation product is different than carbon monoxide, carbon dioxide, and a mixture thereof. Of course, small amounts of these compounds may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane. Other examples include, but are not limited to formation of benzoic acid, phthalic acid, isophthalic acid, and terephthalic acid from toluene, ortho-xylene, meta-xylene, and para-xylene, respectively.

Regarding adipic acid, the preparation of which is especially suited to the methods and devices of this invention, general information may be found in a plethora of U.S. Patents, among other references. These, include, but are not limited to: U.S. Pat. Nos. 2,223,493; 2,589,648; 2,285,914; 3,231,608; 3,234,271; 3,361,806; 3,390,174; 3,530,185; 3,649,685; 3.657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of the claims of this invention.

What is claimed is:

1. A method of controlling in a first reaction zone the oxidation of a hydrocarbon to form an acid in a continuous manner, in the presence of a catalyst, a solvent, an optional initiator, water, and oxidation products; the hydrocarbon, the catalyst, the solvent, and at least part of the oxidation products forming at least partially a liquid mixture, the method characterized by the steps of:

(a) contacting the liquid mixture with a gaseous oxidant in the first reaction zone at a first temperature, the first temperature being adequately high for the oxidation to proceed;

(b) driving the oxidation to a steady state at a first hydrocarbon level, a first solvent level, a first catalyst level, and a first water level;

(c) controlling at least one of the first hydrocarbon level, the first solvent level, the first catalyst level, and the first water level, in a manner to cause formation of and/or maintain a single liquid phase in the first reaction zone, regardless of the presence or absence of a solid phase, and if necessary;

(d) making phase-related adjustments to the liquid mixture, the phase-related adjustments being at least partially based on phase formation relationships, when said liquid mixture is at a second temperature, and wherein the phase related adjustments are directed toward formation and/or maintenance of a single liquid phase.

2. A method as defined in claim 1 wherein the second temperature is substantially the same as the first temperature.

3. A method as de fined in claim 1 wherein the second temperature is different than the first temperature.

4. A method as defined in claim 1 wherein the phase related adjustments to the liquid mixture in the first reaction zone are conducted by a variable selected from a group consisting of temperature in the first reaction zone, pressure in the first reaction zone, gaseous oxidant flow rate into the first reaction zone, water flow rate into the first reaction zone, water removal rate from the first reaction zone, catalyst flow rate into the first reaction zone, hydrocarbon flow rate into the first reaction zone, hydrocarbon removal rate from the first reaction zone, solvent flow rate into the first reaction zone, solvent removal rate from the first reaction zone, recycled off-gas flow rate into the first reaction zone, and a combination thereof.

5. A method as defined in claim 1, further comprising a step of determining, one or more of:

a maximum hydrocarbon level, a maximum water level, and a maximum catalyst level, at or over which, the single liquid phase is transformed to two liquid phases; and a minimum solvent level, at or under which, the single liquid phase is transformed to two liquid phases;

under a set of conditions, wherein levels not being determined remain constant.

6. A method as defined in claim 5 wherein the step of determining one or more of the levels, at or over which, the single liquid phase is transformed to two liquid phases, further comprises steps of:

obtaining a sample of a liquid mixture from the first reaction zone; and adding to the sample, hydrocarbon, or water, or catalyst, or a combination thereof, until a second liquid is formed.

7. A method as defined in claim 6 wherein at least one of the first hydrocarbon level, the first water level, and the first catalyst level is controlled to be under the maximum hydrocarbon level, the maximum water level, and the maximum catalyst level, respectively, and the first solvent level is controlled to be maintained over the minimum solvent level.

8. A method as defined in claim 6, further comprising a step of analyzing the sample to obtain compositional data regarding the sample.

9. A method as defined in claim 8, further comprising steps of
comparing compositional data of the sample with one or more of phase diagrams, thermodynamic data bases, flow sheets, computer flow sheet simulations, catalyst precipitation data, energy balances, and experimental data, and a step of making phase related adjustments and/or catalyst precipitation adjustments in order to avoid formation of a second liquid phase, and/or catalyst precipitation, respectively, in the first reaction zone, if the comparison indicates that formation of a second liquid phase and/or catalyst precipitation are being approached.

10. A method as defined in claim 8, further comprising steps of comparing the compositional data of the sample with one or more of the maximum hydrocarbon level, the maximum water level, the maximum catalyst level, and the minimum solvent level, and making phase related adjustments in the first reaction zone, if one or more of the maximum hydrocarbon level, the maximum water level, the maximum catalyst level, and the minimum solvent level, respectively, is being approached.

11. A method as defined in claim 1 wherein one or more of the first hydrocarbon level, the first catalyst level, and a first water level is controlled to be maintained within a majority range, the majority range being a range between a predetermined high majority level and a predetermined low majority level, the high majority level being lower than a maximum level at or over which maximum level a second phase is formed, the low majority level being between the high majority level and an average of the maximum level and a minimum level, at and under which minimum level catalyst precipitates.

12. A method as defined in claim 1 wherein the first water and/or solvent level is controlled to be maintained within a minority range, the minority range being a range between a predetermined low minority level, and a predetermined high minority level, the low minority level being higher than a minimum level at or under which catalyst precipitates, and the high minority level being between the low minority level and an average of the minimum level and a maximum level, at and over which maximum level a second phase is formed.

13. A method as defined in claim 1 wherein the first temperature is controlled by evaporating condensible volatile matter from the reaction zone, and recirculating at least part of the condensible volatile matter to the reaction zone as condensate.

14. A method as defined in claim 1 wherein the acid comprises adipic acid, the hydrocarbon comprises cyclohexane, the solvent comprises acetic acid, the catalyst comprises a cobalt salt, and the optional initiator comprises a compound selected from a group comprising acetaldehyde, cyclohexanone, and a combination thereof.

15. A method as defined in claim 1, further comprising:
a step of controlling at least one level of the first water level, and the first solvent level in a manner to be higher than a respective level, at or under which, catalyst precipitates; and
the first hydrocarbon level, and the first catalyst level to be lower than a respective level, at or over which, catalyst precipitates.

16. A method as defined in claim 15, further comprising steps of:
taking a sample from the first reaction zone;
lowering the temperature of the sample to a predetermined second temperature, and if a second liquid phase is formed at a critical temperature in the range between the first and second temperatures,
either decrease in the first reaction zone the first level of one component selected from a group consisting of hydrocarbon, water, catalyst, and a mixture thereof to a degree that in a new sample a second liquid phase does not form in the range between the first and second temperatures, or
increase in the first reaction zone the first solvent level to a degree that in a new sample a second liquid phase does not form in the range between the first and second temperatures, or
increase in the first reaction zone the first temperature to a third temperature by at least the difference between the critical temperature and the second temperature, or a combination thereof.

17. A method as defined in claim 15 wherein controlling the first water level within the upper and lower limits is based on determining the composition of the single-phase liquid mixture of the first reaction zone, comparing said composition with one or more of phase diagrams, thermodynamic data bases, flow sheets, computer flow sheet simulations, catalyst precipitation data, energy balances, and experimental data, and adding water to the single-phase liquid mixture in the first reaction zone if the lower limit is being approached or removing water from the first reaction zone if the upper limit is being approached.

18. A method as defined in claim 15, further comprising steps of:
taking a sample from the first reaction zone;
confining the sample within a closed cell under adequate pressure to retain the sample in a substantially liquid form;
raising the cell temperature from the first temperature to a higher temperature; and if catalyst precipitates within a predetermined rise in temperature; and
raising the water level or the solvent level in the first reaction zone, or lowering the hydrocarbon level or the catalyst level in the first reaction zone.

19. A method as defined in claim 15, further comprising steps of:
taking a sample from the first reaction zone;
confining the sample within a closed cell under adequate pressure to retain the sample in a substantially liquid form;
adding hydrocarbon to the sample to determine if catalyst precipitates before formation of a second phase; and
controlling in the first reaction zone the first hydrocarbon level to be maintained at a level lower than the level required to cause catalyst precipitation at levels of solvent, catalyst, and water present in the cell.

20. A method as defined in claim 1, further comprising steps of:
lowering the first temperature to a second temperature, while maintaining a single liquid phase at the second temperature; and
removing at least part of the formed acid.

21. A method as defined in claim 20, further comprising the step of recycling at least part of one or more of products, intermediates, by-products, reactants, solvents, off-gases, and other existing ingredients either directly to the first reaction zone or indirectly after post-treatment, or a combination thereof.

22. A method as defined in claim 20 wherein the lowering of the first temperature to the second temperature is performed at least partially by an operation selected from a group consisting of (a) evaporating of at least part of the hydrocarbon, (b) lowering the first pressure to a second pressure, (c) adding matter having a temperature lower than the first temperature, (d) adding volatile matter, (e) removing heat by external means, (f) removing a first amount of heat by any suitable means, and adding a second amount of heat by external means, the first amount of heat being greater than the second amount of heat, and (g) a combination thereof.

23. A method as defined in claim 20 wherein maintaining a single liquid phase at the second temperature is controlled by adjusting the level of hydrocarbon, or water, or solvent, or a combination thereof, at the second temperature.

24. A method as defined in claim 20 wherein lowering of the first temperature to a second temperature is conducted in a second zone.

25. A method as defined in claim 20, 21, 22, 23; or 24 wherein the lowering of the first temperature to the second temperature involves an intermediate step of lowering the first temperature to a first intermediate temperature by lowering the first pressure to an intermediate pressure to form a first intermediate liquid phase containing no substantial amount of solid phase.

26. A reactor device for oxidizing a hydrocarbon, the hydrocarbon being at least partially in a liquid state, with a gaseous oxidant to form an acid, the device comprising:
a first reaction chamber;
a temperature monitor connected to the reaction chamber for measuring temperature inside said reaction chamber;
phase detection means for detecting phase-related characteristics of ingredients within the first reaction chamber; and
phase control means for making phase-related adjustments and controlling the phase characteristics of said ingredients within the first reaction chamber, if so desired.

27. A reactor device as defined in claim 26 wherein the phase control means further comprise temperature control means for controlling the first temperature.

28. A reactor device as defined in claim 27 wherein the phase control means further comprise correlation means for correlating compositional data of the liquid mixture with one or more of phase diagrams, thermodynamic data bases, flow sheets, computer flow sheet simulations, catalyst precipitation data, energy balances, and experimental data, and making phase related adjustments and/or catalyst precipitation adjustments in order to avoid formation of a second liquid phase, and/or catalyst precipitation, respectively, in the first reaction zone, if the correlation indicates that formation of a second liquid phase and/or catalyst precipitation are being approached.

29. A reactor device as defined in claim 26 wherein the phase detection means provides information to the phase control means for adjusting feeding rates of ingredients fed to the reaction chamber toward formation or maintenance of a single liquid phase.

30. A reactor device as defined in claim 26, further comprising variable control means for controlling in the reaction chamber a variable selected from a group consisting of temperature in the first reaction chamber, pressure in the first reaction chamber, gaseous oxidant flow rate into the first reaction chamber, water flow rate into the first reaction chamber, water removal rate from the first reaction chamber, catalyst flow rate into the first reaction chamber, hydrocarbon flow rate into the first reaction chamber, hydrocarbon removal rate from the first reaction chamber, solvent flow rate into the first reaction chamber, solvent removal rate from the first reaction chamber, recycled off-gas flow rate into the first reaction chamber, and a combination thereof.

31. A reactor device as defined in claim 26, further comprising:
liquid feeding means for feeding at least partially hydrocarbon, solvent, catalyst, optionally initiator, and optionally water into the first reaction chamber;
water removing means for removing water from the first reaction chamber;
gaseous feeding means for feeding oxidant into the first reaction chamber; and
water level control means for controlling the water level in the reaction chamber in a range between a maximum level of water, over which maximum level the substantially single liquid phase is transformed to two liquid phases, and a minimum level under which catalyst precipitates.

32. A reactor device as defined in claim 31 wherein the water level control means comprise water level detection means for detecting positioning of the water level with respect to the maximum level and the minimum level.

33. A reactor device as defined in claim 32, further comprising a controller connected to the water level detection means for receiving information regarding the positioning of the water level, and using said information for adjusting said water level in a manner to control said water level between the maximum level and the minimum level in the reaction zone.

34. A reactor device as defined in claim 32 wherein the water level detection means comprise a temperature operated detector for detecting the positioning of the water level with respect to the minimum level.

35. A reactor device as defined in claim 32 wherein the water level detection means comprise a water-addition operated detector for detecting the positioning of the water level with respect to the maximum level.

36. A reactor device as defined in claim 32 wherein the water level control means comprises an analytical water level detection means for detecting and/or determining the water level in the first reaction chamber, and wherein the reactor device further comprises a controller connected to the analytical water level detection means for receiving information regarding the water level in the reaction chamber, comparing said information with one or more of phase diagrams, thermodynamic data bases, flow sheets, computer flow sheet simulations, catalyst precipitation data, energy balances, and experimental data stored in the controller, and using said comparison for adjusting said water level in the first reaction chamber in a manner to control said water level between the maximum level and the minimum level.

37. A reactor device as defined in claim 31, further comprising a distillation column connected to the first reaction chamber.

38. A reactor device as defined in claim 31, further comprising a condenser connected to the first reaction chamber and a decanter connected to the condenser.

39. A reactor device as defined in claim 32 wherein the water level detection means comprise a temperature operated detector for detecting the positioning of the water level with respect to the minimum level.

40. A reactor device as defined in claim 26, further comprising:

first temperature control means connected to the first reaction chamber for controlling temperature in said first reaction chamber;

first pressure control means connected to the first reaction chamber for controlling pressure in said first reaction chamber;

first hydrocarbon feeding means connected to the first reaction chamber for feeding hydrocarbon into said first reaction chamber;

first gaseous oxidant feeding means connected to the first reaction chamber for feeding gaseous oxidant into said first reaction chamber;

a second chamber connected to the first reaction chamber;

second temperature control means connected to the second chamber for controlling the temperature in said second chamber;

second pressure control means connected to the second chamber for controlling the pressure in said second chamber;

a controller for controlling miscellaneous parameters in the chambers in a manner that in the second chamber there is a single liquid phase.

41. A reactor device as defined in claim 40, further comprising a condenser or distillation column connected to one or both the first reaction chamber and the second chamber.

42. A reactor device as defined in claim 41, further comprising a retaining chamber or decanter connected to the condenser.

43. A reactor device as defined in claim 41, further comprising:

a first intermediate chamber communicating with the first reaction chamber;

first intermediate temperature control means connected to the first intermediate chamber for controlling the temperature in said first intermediate chamber;

first intermediate pressure control means connected to the intermediate chamber for controlling the pressure in said first intermediate chamber;

first intermediate external heating means for providing thermal energy to matter inside the first intermediate chamber;

a condenser connected to the first intermediate chamber;

separating means connected to or being part of the second chamber for separating at least partially the dibasic acid from the mixture.

44. A reactor device as defined in claim 43, further comprising:

a second intermediate chamber connected to the first intermediate chamber and the second chamber;

second intermediate external cooling means for removing thermal energy from matter inside the second intermediate chamber.

45. A reactor device as defined in claim 40, further comprising second phase control means connected to the second chamber for ensuring the existence of one single liquid phase in said second chamber.

46. A reactor device as defined in claim 40, further comprising catalyst precipitation control means connected to the second chamber for ensuring the absence of precipitated catalyst in said second chamber.

47. A reactor device as defined in claim 40, wherein at least two of the chambers constitute one and the same unit.

48. A reactor device as defined in claim 26, comprising an atomization chamber.

49. A reactor device as defined in claim 26, comprising a stirred-tank reactor.

50. A method as defined in claim 1, further comprising a step of comparing compositional data of the liquid mixture with one or more of phase diagrams, thermodynamic data bases, flow sheets, computer flow sheet simulations, catalyst precipitation data, energy balances, and experimental data, and a step of making phase related adjustments and/or catalyst precipitation adjustments in order to avoid formation of a second liquid phase, and/or catalyst precipitation, respectively, in the first reaction zone, if the comparison indicates that formation of a second liquid phase and/or catalyst precipitation are being approached.

51. A method as defined in claim 2, further comprising a step of comparing compositional data of the liquid mixture with one or more of phase diagrams, thermodynamic data bases, flow sheets, computer flow sheet simulations, catalyst precipitation data, energy balances, and experimental data, and a step of making phase related adjustments and/or catalyst precipitation adjustments in order to avoid formation of a second liquid phase, and/or catalyst precipitation, respectively, in the first reaction zone, if the comparison indicates that formation of a second liquid phase and/or catalyst precipitation are being approached.

52. A method as defined in claim 3, further comprising a step of comparing compositional data of the liquid mixture with one or more of phase diagrams, thermodynamic data bases, flow sheets, computer flow sheet simulations, catalyst precipitation data, energy balances, and experimental data, and a step of making phase related adjustments and/or catalyst precipitation adjustments in order to avoid formation of a second liquid phase, and/or catalyst precipitation, respectively, in the first reaction zone, if the comparison indicates that formation of a second liquid phase and/or catalyst precipitation are being approached.

53. A method as defined in claim 4, further comprising a step of comparing compositional data of the liquid mixture with one or more of phase diagrams, thermodynamic data bases, flow sheets, computer flow sheet simulations, catalyst precipitation data, energy balances, and experimental data, and a step of making phase related adjustments and/or catalyst precipitation adjustments in order to avoid formation of a second liquid phase, and/or catalyst precipitation, respectively, in the first reaction zone, if the comparison indicates that formation of a second liquid phase and/or catalyst precipitation are being approached.

54. A method as defined in claim 14, further comprising a step of reacting the adipic acid with a reactant selected from a group consisting of a polyol, a polyamine, and a polyamide in a manner to form a polymer of a polyester, or a polyamide, or a (polyimide and/or poyamideimide), respectively.

55. A method as defined in claim 54, further comprising a step of spinning the polymer into fibers.

56. A method as defined in claim 17 wherein the acid comprises adipic acid, the hydrocarbon comprises cyclohexane, the solvent comprises acetic acid, the catalyst comprises a cobalt salt, and the optional initiator comprises a compound selected from a group comprising acetaldehyde, cyclohexanone, and a combination thereof.

57. A method as defined in claim 56, further comprising a step of reacting the adipic acid with a reactant selected from a group consisting of a polyol, a polyamine, and a polyamide in a manner to form a polymer of a polyester, or a polyamide, or a (polyimide and/or poyamideimide), respectively.

58. A method as defined in claim 57, further comprising a step of spinning the polymer into fibers.

* * * * *

UNITED STATES PATENT AND TRADEMARK OFFICE
CERTIFICATE OF CORRECTION

PATENT NO.    : 6,359,011 B1
DATED         : March 19, 2002
INVENTOR(S)   : Bess et al.

It is certified that error appears in the above-identified patent and that said Letters Patent is hereby corrected as shown below:

Column 18,
Line 10, "asime" should read -- amine --.

Signed and Sealed this

Twenty-fourth Day of September, 2002

Attest:

Attesting Officer

JAMES E. ROGAN
Director of the United States Patent and Trademark Office